(12) United States Patent
Fujdala et al.

(10) Patent No.: US 9,404,002 B2
(45) Date of Patent: Aug. 2, 2016

(54) MOLECULAR PRECURSOR COMPOUNDS FOR INDIUM GALLIUM ZINC OXIDE MATERIALS

(71) Applicant: Precursor Energetics, Inc., Santa Clara (CA)

(72) Inventors: Kyle L. Fujdala, San Jose, CA (US); Christopher Melton, Sunnyvale, CA (US)

(73) Assignee: Transtron Solutions LLC, San Jose, CA (US)

( * ) Notice: Subject to any disclaimer, the term of this patent is extended or adjusted under 35 U.S.C. 154(b) by 0 days.

(21) Appl. No.: 14/174,783

(22) Filed: Feb. 6, 2014

(65) Prior Publication Data

US 2015/0218400 A1    Aug. 6, 2015

(51) Int. Cl.

| | |
|---|---|
| *C09D 11/52* | (2014.01) |
| *H01L 29/24* | (2006.01) |
| *C07F 19/00* | (2006.01) |
| *C08K 5/04* | (2006.01) |
| *H01L 29/786* | (2006.01) |
| *C08K 5/56* | (2006.01) |
| *C07F 5/00* | (2006.01) |
| *C01G 9/00* | (2006.01) |
| *C01G 15/00* | (2006.01) |
| *H01L 27/12* | (2006.01) |
| *C07F 3/06* | (2006.01) |

(52) U.S. Cl.
CPC ................ *C09D 11/52* (2013.01); *C01G 9/006* (2013.01); *C01G 15/00* (2013.01); *C01G 15/006* (2013.01); *C07F 3/06* (2013.01); *C07F 5/003* (2013.01); *C07F 19/005* (2013.01); *C08K 5/56* (2013.01); *H01L 27/1292* (2013.01); *H01L 29/24* (2013.01); *H01L 29/7869* (2013.01); *C01P 2006/88* (2013.01)

(58) Field of Classification Search
None
See application file for complete search history.

(56) References Cited

U.S. PATENT DOCUMENTS

| | | | |
|---|---|---|---|
| 2007/0154561 A1* | 7/2007 | Takeda | A61K 8/19 424/489 |
| 2009/0206746 A1 | 8/2009 | Seo | |
| 2010/0068382 A1* | 3/2010 | Strobel | B05D 3/08 427/255.6 |
| 2011/0146790 A1* | 6/2011 | Fujdala | C07F 5/00 136/258 |
| 2013/0101867 A1 | 4/2013 | Yukinobu | |

FOREIGN PATENT DOCUMENTS

| | | |
|---|---|---|
| WO | 2013157715 A1 | 10/2013 |
| WO | 2013159864 A1 | 10/2013 |
| WO | 2013172949 A1 | 11/2013 |
| WO | 2013190992 A1 | 12/2013 |

* cited by examiner

*Primary Examiner* — Harold Pyon
*Assistant Examiner* — Katie L Hammer
(74) *Attorney, Agent, or Firm* — Eckman Basu LLP

(57) ABSTRACT

Molecular precursor compounds, compositions, inks and processes for making IGZO materials. Inks made from molecular precursor compounds having the empirical formula $In_bGa_cZn(OROR)_{3(b+c)+2}$ can be printed or deposited on a substrate. The printed or deposited film can be treated to convert the molecular precursor compounds to an IGZO material.

25 Claims, 7 Drawing Sheets

MOLECULAR PRECURSOR COMPOUNDS FOR INDIUM GALLIUM ZINC OXIDE MATERIALS

BACKGROUND

Useful candidates for thin film semiconductor and conductor layers for thin-film transistor (TFT) applications include indium gallium zinc oxide (IGZO).

IGZO is used in the TFT backplane of flat-panel displays and monitors. IGZO has higher electron mobility than amorphous silicon and can provide large, high resolution displays with reduced energy requirements.

Significant drawbacks in the production of thin film transistors using these materials are slow manufacturing process speed and throughput, as well as non-uniformity of the composition of deposited layers. These drawbacks are mainly due to the vacuum deposition methods used in the conventional production of thin film transistors.

For example, large scale manufacturing of TFTs, transparent thin-film transistors (TTFTs) and related thin film devices using conventional vacuum-based processes can be unpredictable because of the difficulty in controlling numerous chemical and physical parameters involved in forming a semiconductor or conductor layer of suitable quality on a substrate, both reproducibly and in high yield.

Attempts to increase the efficiency and speed of manufacturing TFT/TTFT materials include use of liquid deposition/printing methods in which particles or precursors for the materials are deposited from an ink. However, ink compositions using components made by sol-gel processes, or that contain nanoparticles, can have drawbacks because they lack stability and compositional uniformity. Their instability is due to the formation of aggregates, particulates or precipitates that cause clogging, blocking or constriction of printing equipment.

Another drawback in the production of thin film transistors is the inability to control the stoichiometry of the product materials. With existing methods and approaches, many useful material compositions are difficult to make because of the lack of control of the stoichiometry. A significant problem is the need to create thin films of semiconducting and conducting materials with controlled compositional homogeneity, uniformity and purity.

There is a long-standing need for solution-based processes for making semiconducting and conducting materials having a predetermined stoichiometry for thin film applications.

There is a need for stable ink compositions having molecular precursor compounds that are completely soluble so that the ink can be used in a high speed and high yield printing process for making semiconducting and conducting materials for thin film transistors.

What is needed are compounds and compositions to produce semiconducting and conducting materials from solution-based processes for thin film transistors, display devices and other products.

BRIEF SUMMARY

This invention provides a range of compositions and processes used to make indium gallium zinc oxide (IGZO) materials.

This invention relates to compounds, compositions and processes used to make IGZO materials for thin film transistors. In particular, this invention relates to molecular precursor compounds, compositions and processes for making thin film transistors by ink deposition.

Embodiments of this invention include molecular precursor compounds, which can be used in manufacturing thin film transistors in processes with high speed and throughput. Processes of this disclosure can involve solution-based deposition instead of vacuum deposition methods. This invention provides molecular precursor compounds, inks thereof, and processes for making thin film transistor materials with compositional uniformity of deposited layers.

Embodiments of this invention further provide liquid deposition/printing methods in which precursors for materials are deposited from an ink. Ink compositions of this disclosure can be stable and lack particulates or precipitates that cause clogging, blocking or constriction of printing equipment.

In further aspects, the molecular precursor compounds, inks, and processes of this invention allow control of the stoichiometry of the product materials. Materials having a predetermined stoichiometry can be made from molecular precursor compounds of predetermined stoichiometry.

This invention provides ink compositions made from molecular precursor compounds that are completely soluble so that the ink can be used in a high speed and high yield deposition/printing process for making materials for thin film transistors.

Embodiments of this disclosure include:

A molecular precursor compound having the empirical formula $In_bGa_cZn(OROR)_{3(b+c)+2}$, wherein b and c are each independently from 0.01 to 9.99, the sum of b+c is from 0.02 to 10, and each R is independently alkyl or aryl.

The compound above, wherein the R groups are independently selected, for each occurrence, from C(1-6)alkyl groups. The compound above, wherein the R groups are independently selected, for each occurrence, from ethyl, n-propyl, isopropyl, n-butyl, sec-butyl, isobutyl, t-butyl, isopentyl, 2-methylbutyl, 3-methylbutyl, 2,2-dimethylbutyl, 2,3-dimethylbutyl, 2-methylpentyl, 3-methylpentyl, and 4-methylpentyl. The compound above, wherein the R groups are independently selected, for each occurrence, from C(2-4)alkyl groups.

An ink comprising a molecular precursor compound above and one or more solvents. The ink above, wherein the ink further comprises one or more dopant elements selected from halides, Mg, Y, Ti, Zr, Nb, Cr, Ru, Bi, Sb, and La.

A process for making a material, the process comprising: providing an ink comprising one or more molecular precursor compounds above; depositing the ink on a substrate; and heating the substrate.

The process above, wherein the ratio of (In+Ga) to Zn in the ink is from 0.02 to 10. The process above, wherein the heating is at a temperature of from 50° C. to 500° C. The process above, wherein the heating is performed in air having controlled humidity. The process above, wherein the depositing is done with an ink by printing, inkjet printing, aerosol jet printing, gravure printing, reverse gravure printing, reverse offset gravure printing, stamp printing, transfer printing, pad printing, spray pattern printing, flexographic printing, contact printing, reverse printing, thermal printing, lithography, electrophotographic printing, screen printing, spraying, spray coating, spray deposition, spray pyrolysis, coating, dip coating, wet coating, spin coating, knife coating, roller coating, rod coating, slot die coating, meyerbar coating, lip direct coating, capillary coating, liquid deposition, solution deposition, layer-by-layer deposition, spin casting, and solution casting. The process above, wherein the substrate is a glass, a ceramic, or a polymer. A material made by the process above. A thin film transistor comprising the material above.

A process for making a material, the process comprising: providing an ink comprising dissolving monomer compounds $Zn(Q)_2$, $In(Q)_3$, and $Ga(Q)_3$, wherein Q is —OROR, and wherein each R is independently alkyl or aryl; depositing the ink on a substrate; and heating the substrate.

The process of above, wherein the ratio of the sum of (In+Ga) to Zn in the ink is from 0.02 to 10. The process above, wherein the R groups are independently selected, for each occurrence, from C(1-6)alkyl groups. The process above, wherein the R groups are independently selected, for each occurrence, from ethyl, n-propyl, isopropyl, n-butyl, sec-butyl, isobutyl, t-butyl, isopentyl, 2-methylbutyl, 3-methylbutyl, 2,2-dimethylbutyl, 2,3-dimethylbutyl, 2-methylpentyl, 3-methylpentyl, and 4-methylpentyl. The process above, wherein the R groups are independently selected, for each occurrence, from C(2-4)alkyl groups. The process above, wherein the heating is at a temperature of from 50° C. to 500° C. The process above, wherein the heating is performed in air having controlled humidity. The process above, wherein the ink further comprises one or more dopant elements selected from halides, Mg, Y, Ti, Zr, Nb, Cr, Ru, Bi, Sb, and La. The process above, wherein the substrate is a glass, a ceramic, or a polymer. A material made by the process above. A thin film transistor comprising the material above.

DETAILED DESCRIPTION

Figure 1:
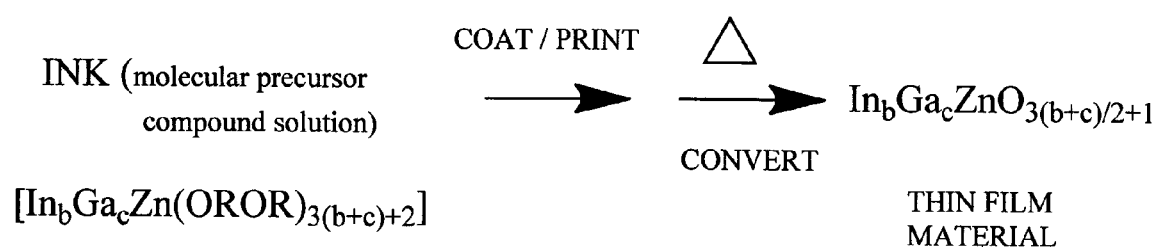
FIG. 1 shows a diagram of an embodiment of this invention in which IGZO materials are synthesized from molecular precursor compounds. The molecular precursor compounds can be synthesized, isolated, and used to make inks for printing or depositing on a substrate. The printed or deposited molecular precursor compounds can be converted into a material having a predetermined stoichiometry, represented by the general formula $In_bGa_cZnO_{3(b+c)/2+1}$.

This invention provides compounds, compositions and processes for making indium gallium zinc oxide (IGZO) materials.

In one aspect, this disclosure provides processes to make IGZO materials such as IGZO using soluble molecular precursor compounds. The molecular precursor compounds can be converted to high quality IGZO materials with controlled stoichiometry. Thus, this invention provides processes using molecular precursor compounds that can be used for facile synthesis of IGZO materials of particular predetermined stoichiometry.

Processes using molecular precursor compounds of this disclosure can be used to synthesize IGZO materials for thin film transistors. The molecular precursor compounds of this disclosure may be soluble or solubilized, so that solution, ink and printing processes may be performed. The molecular precursors of this invention can be advantageously soluble in one or more organic solvents.

Embodiments of this invention provide soluble molecular precursor compounds that can be completely dissolved and used in a solution-based process without aggregates or particulates. The surprising solubility of the molecular precursor compounds of this invention provides inks for direct pattern printing for making IGZO materials for displays, thin film transistors, solar cells and other devices.

The molecular precursor compounds of this disclosure can be in solid form, or in liquid form.

The molecular precursor compounds of this disclosure can be dissolved in an organic solvent or solvent mixture without forming particles or nanoparticles. Inks of this invention can advantageously be used for efficiently printing a thin film on a substrate, so that the film can be converted into a thin film material. The molecular precursor compounds of this disclosure can be surprisingly soluble in an organic solvent or solvent mixture.

This disclosure provides solution-based processes for making IGZO materials having a predetermined stoichiometry for thin film TFT, and other products and applications.

This invention provides stable ink compositions composed of molecular precursor compounds that are completely soluble. Inks of this invention can be used in high speed and high yield printing process for making oxide materials for thin film transistors.

Embodiments of this invention further provide compounds and compositions for making IGZO oxide materials using solution-based processes for thin film transistors, display devices and other products.

Molecular precursor compounds and compositions of this invention can advantageously be used to make homogeneous IGZO materials at moderate temperatures, and for synthesis of IGZO materials with controlled stoichiometry.

In some embodiments, molecular precursor compounds and compositions of this invention can advantageously be used to make amorphous IGZO materials at moderate temperatures and with controlled stoichiometry.

In additional embodiments, the IGZO materials made with compounds and compositions of this invention can be further treated and transformed into crystalline or semicrystalline forms.

In further embodiments, molecular precursor compounds and compositions of this invention can advantageously be used to make crystalline IGZO materials at moderate temperatures and with controlled stoichiometry.

The molecular precursor compounds of this invention can also be used to make thin film transistors. Thin film layers can be made by depositing molecular precursor compounds and transforming the deposited layer into a material.

Solutions and inks made from molecular precursor compounds of this disclosure may be used to make IGZO materials in thin film forms useful for making thin film transistors.

Processes of this invention can employ one or more molecular precursor compounds, or inks thereof, to make IGZO materials having a predetermined stoichiometry.

Processes using molecular precursor compounds of this invention can advantageously provide IGZO materials having a predetermined stoichiometry of the ratio of zinc to atoms of Group 13. Controlling the ratios In/Ga, In/Zn and Ga/Zn in processes of this invention advantageously provides targeted compositions for IGZO materials.

In general, the structure and properties of the molecular precursor compounds and ink compositions of this invention provide advantages in making thin film transistors and devices regardless of the morphology, architecture, or manner of fabrication of the devices.

Isolated Molecular Precursor Compounds

This invention provides a range of isolated molecular precursor compounds. A molecular precursor compound of this invention can contain a zinc atom along with In and Ga atoms bound in the same precursor compound. In general, the molecular precursor compound has, within its compositional structure, both a zinc atom and atoms of Group 13, which can be connected to the zinc atom via oxygen atoms. The atoms of Group 13 can also be connected to other atoms of Group 13 via oxygen atoms. Without wishing to be bound by any particular theory, the presence of both a zinc atom and atoms of Group 13 provides pre-existing Group 13 atom-oxygen-zinc atom linkages to facilitate production of IGZO materials with high compositional uniformity.

The molecular precursor compounds can be isolated and stored for use in various processes for printing or depositing the compounds on a substrate. For example, the isolated molecular precursor compounds can be dissolved in one or more solvents to form an ink. Inks can be used for printing or depositing layers of one or more molecular precursor compounds which can be converted to a IGZO material.

It can be emphasized that molecular precursor compounds of this invention, as described in this section, can be isolated, and later used to make target materials of predetermined stoichiometry in the ratio of Group 13 atoms to zinc atoms. The ratio of Group 13 atoms to zinc atoms in target materials can be predetermined by using ink compositions made from a molecular precursor compound having the predetermined ratio of Group 13 atoms to zinc atoms in the desired target material.

This invention provides processes, compounds and compositions that can advantageously be used to make IGZO materials with a controlled ratio of In/Ga, In/Zn, and Ga/Zn.

In any formula of this disclosure, each R group can be independently selected from alkyl and aryl.

In some embodiments, an —OROR groups can be independently selected, for each occurrence, from alkoxyalkoxy, aryloxyalkoxy, heteroaryloxyalkoxy, and alkenyloxyalkoxy.

A molecular precursor compound may be crystalline, or non-crystalline.

In certain embodiments, an IGZO molecular precursor compound can have the empirical formula $In_b Ga_c Zn(OROR)_{3(b+c)+2}$, which is a compound having atoms of indium, gallium, and zinc, and —OROR groups, where b and c are independently from 0.01 to 9.99, and the sum of b+c is from 0.02 to 10. In some embodiments, b and c are independently from 0.05 to 4.95, and the sum of b+c is from 0.1 to 5. In some embodiments, b and c are independently from 0.25 to 3.75, and the sum of b+c is from 0.5 to 4. These molecular precursor compounds can also be represented as $In_b(OROR)_{3b} Ga_c(OROR)_{3c} Zn(OROR)_2$, where the R and —OROR groups are as defined above.

Examples of IGZO molecular precursor compounds include $In_{0.46}Ga_{0.04}Zn(OCH_2CH_2O^iPr)_{3.5}$, $In_{0.46}Ga_{0.04}Zn(OCH_2CH_2O^tBu)_{3.5}$, $In_{0.46}Ga_{0.04}Zn(OCH(CH_3)CH_2O^sBu)_{3.5}$, $In_{0.7}Ga_{0.3}Zn(OCH_2CH_2O^sBu)_5$, $In_{0.7}Ga_{0.3}Zn(OCH_2CH_2O^tBu)_5$, $In_{0.7}Ga_{0.3}Zn(OCH(CH_3)CH_2O^tBu)_5$, $In_{0.38}Ga_{0.7}Zn(OCH_2CH_2O^iPr)_{5.24}$, $In_{0.38}Ga_{0.7}Zn(OCH_2CH_2O^tBu)_{5.24}$, $In_{0.38}Ga_{0.7}Zn(OCH(CH_3)CH_2O^tBu)_{5.24}$, $In_{1.0}Ga_{0.5}Zn(OCH_2CH_2O^iPr)_{6.5}$, $In_{1.0}Ga_{0.5}Zn(OCH_2CH_2O^tBu)_{6.5}$, $In_{1.0}Ga_{0.5}Zn(OCH(CH_3)CH_2O^tBu)_{6.5}$, $InGaZn(OCH_2CH_2O^iPr)_8$, $InGaZn(OCH_2CH_2O^tBu)_8$, $InGaZn(OCH(CH_3)CH_2O^tBu)_8$, $InGaZn(OCH(CH_3)CH_2O^tBu)_4(OEtO^iPr)_4$, $InGa_{1.1}Zn(OCH_2CH_2O^iPr)_{8.3}$, $InGa_{1.1}Zn(OCH_2CH_2O^tBu)_{8.3}$, $InGa_{1.1}Zn(OCH(CH_3)CH_2O^tBu)_{8.3}$, $In_{1.7}Ga_{0.5}Zn(OCH_2CH_2CH_2O^iPr)_{8.6}$, $In_{1.7}Ga_{0.5}Zn(OCH_2CH_2CH_2O^tBu)_{8.6}$, $In_{1.7}Ga_{0.5}Zn(OCH(CH_3)CH_2O^tBu)_{8.6}$, $In_{1.9}Ga_{0.5}Zn(OCH_2CH_2CH_2O^iPr)_{9.2}$, $In_{1.02}Ga_{1.52}Zn[OCH_2CH_2OCH(CH_3)_2]_{9.62}$, $In_{1.9}Ga_{0.5}Zn(OCH_2CH_2CH_2O^tBu)_{9.2}$, $In_{1.9}Ga_{0.5}Zn(OCH(CH_3)CH_2O^tBu)_{9.2}$, $In_{1.9}Ga_{0.95}Zn[OCHCH_3CH_2OC(CH_3)_3]_{8.55}[OCH_2CH_2OCH(CH_3)_2]_2$, $In_{2.0}Ga_{0.97}Zn(OCH_2CH_2O^iPr)_{10.91}$, $In_{2.0}Ga_{0.97}Zn(OCH_2CH_2O^tBu)_{10.91}$, $In_{2.0}Ga_{0.97}Zn(OCH(CH_3)CH_2O^tBu)_{10.91}$, $In_{2.0}Ga_{1.1}Zn(OCH_2CH_2O^iPr)_{11.3}$, $In_{2.0}Ga_{1.1}Zn(OCH_2CH_2O^tBu)_{11.3}$, $In_2GaZn(OCH(CH_3)CH_2O^tBu)_{11}$, $In_2GaZn(OCH(CH_3)CH_2O^tBu)_6(OEtO^iPr)_5$, $In_{2.0}Ga_{1.1}Zn(OCH(CH_3)CH_2O^tBu)_{11.3}$, $In_{0.53}Ga_{2.58}Zn(OCH_2CH_2O^iPr)_{11.33}$, $In_{0.53}Ga_{2.58}Zn(OCH_2CH_2O^tBu)_{11.33}$, $In_{0.53}Ga_{2.58}Zn(OCH(CH_3)CH_2O^tBu)_{11.33}$, $In_{2.21}Ga_{1.06}Zn(OCH_2CH_2O^iPr)_{11.81}$, $In_{2.21}Ga_{1.06}Zn(OCH_2CH_2O^tBu)_{11.81}$, $In_{2.21}Ga_{1.06}Zn(OCH(CH_3)CH_2O^tBu)_{11.81}$, $In_{2.2}Ga_{1.8}Zn(OCH(CH_3)CH_2O^tBu)_{14}$, $In_{3.5}Ga_{2.5}Zn(OCH_2CH_2O^tBu)_{20}$, $In_4Ga_{3.5}Zn(OCH(CH_3)CH_2O^tBu)_{24.5}$, and $In_5Ga_4Zn(OCH(CH_3)CH_2O^tBu)_{27}$.

Examples and Structures of Molecular Precursor Compounds

In any formula of this disclosure, each R group can be independently selected from alkyl and aryl.

In any formula of this disclosure, an —OROR group can be independently selected, for each occurrence, from alkoxyalkoxy, aryloxyalkoxy, heteroaryloxyalkoxy, and alkenyloxyalkoxy.

The group (OEtO) in any formula herein represents $(OCH_2CH_2O)$. For example, the group $(OEtO^iPr)$ in any formula herein represents $(OCH_2CH_2O^iPr)$, which is $(OCH_2CH_2OCH(CH_3)_2)$.

In some embodiments, a molecular precursor compound of this invention can be isolated in the form of a dimer, trimer, or tetramer, etc. In such cases, the empirical formula of the compound can be written as, for example, $[In_b Ga_c Zn(OROR)_{3(b+c)+2}]_n$, where n is 2, 3, 4 etc. In certain embodiments, n can be from 1 to 100, or more. Such molecules can be referred to as being oligomers, polymers, or mixtures thereof.

A molecular precursor compound of this invention can be an inorganic coordination compound or an inorganic coordination polymer.

In some embodiments, a molecular precursor compound can be represented by the following structure:

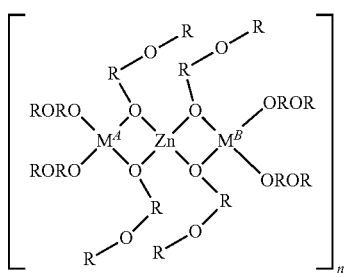

where $M^A$ and $M^B$ are independently selected from In and Ga, groups —OROR are as defined above, and the compound contains indium and gallium.

In some embodiments, a molecular precursor compound can be represented by the following structure:

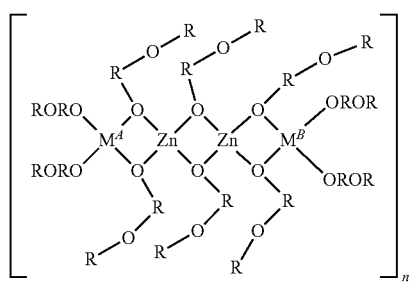

where $M^A$ and $M^B$ are independently selected from In and Ga, groups —OROR are as defined above, and the compound contains indium and gallium.

In the structures above, the compound is polymeric, as indicated by the brackets, and is composed of a chain of n monomer species, where n is 2, 3, 4 etc. In a polymeric precursor compound, monomers are linked to form a polymer chain, whether linear, cyclic, or branched, or of any other shape. The monomers may be arranged in any order. In certain embodiments, n can be from 1 to 100, or more. The polymeric precursor compounds of this invention may be made with any desired stoichiometry regarding the number of zinc atoms and Group 13 atoms.

For each occurrence, an —OROR group can be independently selected from alkoxyalkoxy, aryloxyalkoxy, heteroaryloxyalkoxy, and alkenyloxyalkoxy.

In any formula of this disclosure, each R group can be independently selected, for each occurrence, from C(1-22) alkyl groups. In certain embodiments, R can be independently selected, for each occurrence, from C(1-6)alkyl groups. In certain embodiments, R can be independently selected, for each occurrence, from C(2-6)alkyl groups. In certain embodiments, R can be independently selected, for each occurrence, from C(2-4)alkyl groups. In further embodiments, R can be independently selected, for each occurrence, from ethyl, n-propyl, isopropyl, n-butyl, sec-butyl, isobutyl, t-butyl, isopentyl, 2-methylbutyl, 3-methylbutyl, 2,2-dimethylbutyl, 2,3-dimethylbutyl, 2-methylpentyl, 3-methylpentyl, and 4-methylpentyl.

In any formula of this disclosure, in the formulas above, the R groups can be independently selected, for each occurrence, from phenyl, alkyl substituted phenyl, naphthyl, tetrahydronaphthyl, indanyl, and biphenyl.

Examples of an —OROR group include methoxymethoxide, ethoxymethoxide, (n-propoxy)methoxide, isopropoxymethoxide, (n-butoxy)methoxide, (sec-butoxy)methoxide, (tert-butoxy)methoxide, neopentoxymethoxide, methoxyethoxide, ethoxyethoxide, (n-propoxy)ethoxide, isopropoxyethoxide, (n-butoxy)ethoxide, (sec-butoxy) ethoxide, (tert-butoxy)ethoxide, neopentoxyethoxide, 3-methoxy-1-propoxide, 3-ethoxy-1-propoxide, 3-(n-propoxy)-1-propoxide, 3-isopropoxy-1-propoxide, 3-(n-butoxy)-1-propoxide, 3-(sec-butoxy)-1-propoxide, 3-(tert-butoxy)-1-propoxide, 3-neopentoxy-1-propoxide, 1-methoxy-2-propoxide, 1-ethoxy-2-propoxide, 1-(n-propoxy)-2-propoxide, 1-isopropoxy-2-propoxide, 1-(n-butoxy)-2-propoxide, 1-(sec-butoxy)-2-propoxide, 1-(tert-butoxy)-2-propoxide, 1-neopentoxy-2-propoxide, 4-methoxy-1-butoxide, 4-ethoxy-1-butoxide, 4-(n-propoxy)-1-butoxide, 4-isopropoxy-1-butoxide, 4-(n-butoxy)-1-butoxide, 4-(sec-butoxy)-1-butoxide, 4-(tert-butoxy)-1-butoxide, 4-neopentoxy-1-butoxide, 3-methoxy-2-butoxide, 3-ethoxy-2-butoxide, 3-(n-propoxy)-2-butoxide, 3-isopropoxy-2-butoxide, 3-(n-butoxy)-2-butoxide, 3-(sec-butoxy)-2-butoxide, 3-(tert-butoxy)-2-butoxide, 3-neopentoxy-2-butoxide, 2-methoxy-2-methyl-1-propoxide, 2-ethoxy-2-methyl-1-propoxide, 2-(n-propoxy)-2-methyl-1-propoxide, 2-isopropoxy-2-methyl-1-propoxide, 2-(n-butoxy)-2-methyl-1-propoxide, 2-(sec-butoxy)-2-methyl-1-propoxide, 2-(tert-butoxy)-2-methyl-1-propoxide, 2-neopentoxy-2-methyl-1-propoxide, 3-methoxy-2-methyl-2-propoxide, 3-ethoxy-2-methyl-2-propoxide, 3-(n-propoxy)-2-methyl-2-propoxide, 3-isopropoxy-2-methyl-2-propoxide, 3-(n-butoxy)-2-methyl-2-propoxide, 3-(sec-butoxy)-2-methyl-2-propoxide, 3-(tert-butoxy)-2-methyl-2-propoxide, 3-neopentoxy-2-methyl-2-propoxide, 5-methoxy-1-methyl-2-pentoxide, 5-ethoxy-1-methyl-2-pentoxide, 5-(n-propoxy)-1-methyl-2-pentoxide, 5-isopropoxy-1-methyl-2-pentoxide, 5-(n-butoxy)-1-methyl-2-pentoxide, 5-(sec-butoxy)-1-methyl-2-pentoxide, 5-(tert-butoxy)-1-methyl-2-pentoxide, 5-neopentoxy-1-methyl-2-pentoxide, 5-methoxy-2,4-dimethyl-1-pentoxide, 5-ethoxy-2,4-dimethyl-1-pentoxide, 5-(n-propoxy)-2,4-dimethyl-1-pentoxide, 5-isopropoxy-2,4-dimethyl-1-pentoxide, 5-(n-butoxy)-2,4-dimethyl-1-pentoxide, 5-(sec-butoxy)-2,4-dimethyl-1-pentoxide, 5-(tert-butoxy)-2,4-dimethyl-1-pentoxide, and 5-neopentoxy-2,4-dimethyl-1-pentoxide.

Examples of an —OROR group include methoxymethoxy, methoxyethoxy, methoxypropoxy, methoxyisopropoxy, methoxybutoxy, methoxy(sec-butoxy), methoxy(neo-pentoxy), ethoxymethoxy, ethoxyethoxy, ethoxypropoxy, ethoxyisopropoxy, ethoxybutoxy, ethoxy(sec-butoxy), ethoxy(neo-pentoxy), propoxymethoxy, propoxyethoxy, propoxypropoxy, propoxyisopropoxy, propoxybutoxy, propoxy(sec-butoxy), propoxy(neo-pentoxy), isopropoxymethoxy, isopropoxyethoxy, isopropoxypropoxy, isopropoxyisopropoxy, isopropoxybutoxy, isopropoxy(sec-butoxy), isopropoxy(neo-pentoxy), butoxymethoxy, butoxyethoxy, butoxypropoxy, butoxyisopropoxy, butoxybutoxy, butoxy(sec-butoxy), butoxy(neo-pentoxy), (sec-butoxy)methoxy, (sec-butoxy)ethoxy, (sec-butoxy)propoxy, (sec-butoxy)isopropoxy, (sec-butoxy)butoxy, (sec-butoxy)(sec-butoxy), (sec-butoxy)(neo-pentoxy), (tert-butoxy)methoxy, (tert-butoxy)ethoxy, (tert-butoxy)propoxy, (tert-butoxy)isopropoxy, (tert-butoxy)butoxy, (tert-butoxy)(sec-butoxy), (tert-butoxy)(neo-pentoxy), (neo-pentoxy)methoxy, (neo-pentoxy)ethoxy, (neo-pentoxy)propoxy, (neo-pentoxy)isopropoxy, (neo-pentoxy)butoxy, (neo-pentoxy)(sec-butoxy), and (neo-pentoxy)(neo-pentoxy), and all positional isomers thereof.

As used herein, the terms, for example, ethoxyethoxy and ethoxyethoxide are synonymous.

In general, the structure and properties of the molecular precursor compounds, inks, compositions, and materials of this invention provide advantages in making IGZO materials, as well as thin film transistor devices regardless of the morphology, architecture, or manner of fabrication of the devices.
Monomer Starting Compounds for Molecular Precursor Compounds In some embodiments, a molecular precursor compound can be synthesized by mixing monomer compounds having the formula $In(OROR)_3$, $Ga(OROR)_3$, and a monomer compound having the formula $Zn(OROR)_2$, where the —OROR groups are as defined above.

Referring to FIG. 1, in some embodiments, oxide materials containing zinc and Group 13 atoms can be synthesized by first preparing and isolating molecular precursor compounds of this invention having controlled stoichiometry. The molecular precursor compounds can be synthesized by reacting monomer compound $Zn(Q)_2$ with monomer compounds $In(Q)_3$, and $Ga(Q)_3$. The isolated molecular precursor compounds can be dissolved and formulated in an ink that can be printed or deposited onto a substrate.

In some embodiments, Q is —OROR.

For example, a molecular precursor compound can be deposited and converted into a material having a predetermined stoichiometry represented as $In_bGa_cZnO_{3(b+c)/2+1}$.

In additional aspects, molecular precursor compounds can be deposited and converted into a material having a predetermined stoichiometry in the ratio of atoms represented as In/Ga/Zn. For example, when Zn is 1, each of In and Ga can range from 0.01 to 9.99, where the sum of In+Ga is 10. In some embodiments, when Zn is 1, each of In and Ga can range from 0.05 to 4.95, where the sum of In+Ga is 5.

In some embodiments, IGZO materials can be synthesized by first preparing an ink composition made from $Zn(Q)_2$ and monomer compounds $In(Q)_3$ and $Ga(Q)_3$ of this disclosure. In these embodiments, the molecular precursor compounds are formed in-situ in the ink and do not need to be isolated. The ink composition can have a predetermined stoichiometry of the ratio of zinc to atoms of Group 13. The ink can be printed or deposited as a layer onto a substrate. The deposited layer can be converted into a material having a predetermined stoichiometry as described above, as represented, for example, by the ratio In/Ga/Zn or $In_bGa_cZnO_x$.

In some aspects, a molecular precursor compound can be synthesized by mixing appropriate monomer compounds having the formula $(RO)_yM^4(Q)_{3-y}$, and a monomer compound having the formula $Zn(Q)_2$ or $(RO)Zn(Q)$, where $M^4$ is selected from In and Ga, y is 1 or 2, and Q is as defined above.

Monomer compounds can have the formula $M^4(OROR)_3$, where $M^4$ is selected from In and Ga, and the —OROR groups are as defined above.

In some aspects, a molecular precursor compound can be synthesized by mixing appropriate monomer compounds having the formula $(RO)_yM^4(OROR)_{3-y}$, and a monomer compound having the formula $Zn(OROR)_2$ or $Zn(OR)(OROR)$, where $M^4$ is selected from In and Ga, y is 1 or 2, and the —OROR groups are as defined above.

In some embodiments, an IGZO molecular precursor compound can be synthesized by mixing a monomer compound having the formula $In(OROR)_3$, a monomer compound having the formula $Ga(OROR)_3$, and a monomer compound having the formula $Zn(OROR)_2$, where the —OROR groups are as defined above.

For the compositions above, a molecular precursor compound can be isolated from the mixture. In these embodiments, the mixture composition represents a method for making the isolated molecular precursor compounds.

In some embodiments, the mixtures above can be directly used or deposited to make a product material without isolating the molecular precursor compound. In these embodiments, the mixture compositions represent methods for directly making product materials having controlled and predetermined stoichiometry.

For the compositions above, a molecular precursor compound can be isolated from the mixture. In these embodiments, the mixture composition represents a method for making the isolated molecular precursor compounds.

In some embodiments, the mixtures above can be directly used or deposited to make a product material without isolating the molecular precursor compound. In these embodiments, the mixture compositions represent methods for directly making product materials having controlled and predetermined stoichiometry.

Molecular Precursor Compositions with Controlled Stoichiometry

Embodiments of this invention provide compositions made from components that provide the predetermined stoichiometry of an IGZO target material.

In some embodiments, this invention provides ink compositions made from a molecular precursor compound that provides the predetermined stoichiometry of an IGZO target material.

An ink composition of this disclosure can be a solution of a dissolved molecular precursor compound.

An ink composition of this disclosure can be a solution of one or more dissolved molecular precursor compounds.

An ink composition of this disclosure can be a solution of a dissolved compound, or a solution of one or more dissolved compounds.

An IGZO target material can be prepared by first making a molecular precursor compound that can be isolated in solid or liquid form, or dissolved or solubilized in solution.

In certain embodiments, processes of this invention include depositing an ink composition onto a substrate, or onto a component layer of a transistor.

In some aspects, a thin film transistor can be prepared by first making molecular precursor compounds isolated in solid or liquid form, and dissolving one or more of the molecular precursor compounds in one or more solvents to form an ink composition. An ink may comprise one or more molecular precursor compounds, and one or more inks can be used to synthesize an IGZO material having a predetermined stoichiometry.

A molecular precursor compound may exist in a liquid form under the temperature and conditions used for printing, deposition, or coating.

In certain embodiments, an ink composition can be formed with one or more molecular precursor compounds so that the ink has a controlled stoichiometry of the ratio of a metal to atoms of an element of Group 13. An ink composition having controlled stoichiometry can be used to make a target IGZO material having the same stoichiometry.

Embodiments of this invention provide molecular precursor compounds that are advantageously soluble and can be used in solution-based depositions for making IGZO materials.

In certain embodiments, a thin film transistor can be prepared by providing isolated monomer compounds and dissolving the monomer compounds to form an ink composition, where a molecular precursor compound is formed in the ink. The molecular precursor compound formed in the ink can be isolated from the ink, or can be used directly to make a thin film material.

In further aspects, a molecular precursor compound of this invention can be used in an ink for making IGZO materials. The ink can be prepared with a controlled stoichiometry in any of the ratios In/Zn, Ga/Zn, In/Ga and In/Ga/Zn. The controlled stoichiometry of the ink is due to the controlled stoichiometry of the molecular precursor compound dissolved in the ink. The stoichiometry with respect to atoms of any of In, Ga, and Zn can be predetermined by the molecular precursor compound used to prepare the ink. The ink can be deposited, and the deposited layer converted to form an IGZO material having the predetermined stoichiometry.

Embodiments of this invention further provide compositions and processes for making IGZO materials using ink compositions that include additional molecular precursor compounds and/or monomer compounds.

Target IGZO Materials

A large number of IGZO materials are disclosed herein having a range of compositions. Methods and embodiments of this disclosure can provide a wide range of target IGZO materials having controlled stoichiometry of various atoms.

As used herein, target materials include materials having predetermined stoichiometry that can be made with compounds and compositions of this disclosure having the same predetermined stoichiometry.

Target materials include IGZO materials such as $In_bGa_cZnO_x$, where each of b and c is from 0.01 to 9.99, the sum of b+c is from 0.02 to 10, and x is from 1.03 to 16. In some embodiments, each of b and c is from 0.05 to 4.95, and the sum of b+c is from 0.1 to 5. In some embodiments, each of b and c is independently from 0.25 to 3.75, and the sum of b+c is from 0.5 to 4.

Examples of a target material include $In_bGa_cZnO_{(1+3b/2+3c/2)}$.

Examples of a target material include $In_{0.06}Ga_{0.01}ZnO_{1.105}$, $In_{0.2}Ga_{0.05}ZnO_{1.375}$, $In_{0.2}Ga_{0.1}ZnO_{1.45}$, $In_{0.3}Ga_{0.1}ZnO_{1.6}$, $In_{0.4}Ga_{0.1}ZnO_{1.75}$.

Examples of a target material include $In_{0.7}Ga_{0.3}ZnO_{2.5}$, $In_{0.8}Ga_{0.2}ZnO_{2.5}$, $In_{1.0}Ga_{0.5}ZnO_{3.25}$, $In_{1.1}Ga_{0.4}ZnO_{3.25}$, $In_{1.4}Ga_{0.6}ZnO_4$, $In_{1.5}Ga_{0.5}ZnO_4$, $In_{1.1}Ga_{0.9}ZnO_4$, $In_{1.2}Ga_{0.8}ZnO_4$, $In_{1.5}GaZnO_{4.75}$, $In_{1.7}Ga_{0.8}ZnO_{4.75}$, $In_{1.5}GaZnO_{4.75}$, $In_{1.8}Ga_{0.7}ZnO_{4.75}$, $In_{2.0}Ga_{0.5}ZnO_{4.75}$, $In_{2.2}Ga_{0.3}ZnO_{4.75}$, $In_{2.0}GaZnO_{5.5}$, $In_{2.3}Ga_{0.7}ZnO_{5.5}$, $In_{2.5}GaZnO_{6.25}$, $In_{2.8}Ga_{0.7}ZnO_{6.25}$, $In_{2.5}GaZnO_{6.25}$, $In_{2.9}Ga_{0.6}ZnO_{6.25}$, $In_{2.0}Ga_{1.5}ZnO_{6.25}$, $In_{2.2}Ga_{1.3}ZnO_{6.25}$, $In_3GaZnO_7$, $In_{3.2}Ga_{0.8}ZnO_7$, $In_2Ga_2ZnO_7$, $In_{2.3}Ga_{1.7}ZnO_7$, and $In_3GaZnO_7$.

Examples of a target material include $In_4GaZnO_{8.5}$, $In_{4.5}Ga_{0.5}ZnO_{8.5}$, $In_5GaZnO_{10}$, $In_{5.5}Ga_{0.5}ZnO_{10}$, $In_6GaZnO_{11.5}$, $In_{6.5}Ga_{0.5}ZnO_{11.5}$, $In_7GaZnO_{13}$, $In_{7.5}Ga_{0.5}ZnO_{13}$, $In_8GaZnO_{14.5}$, and $In_{8.5}Ga_{0.5}ZnO_{14.5}$.

The examples above are not to be taken as limiting the invention.

Thin Film Transistor (TFT/TTFT) Devices

Figure 2:
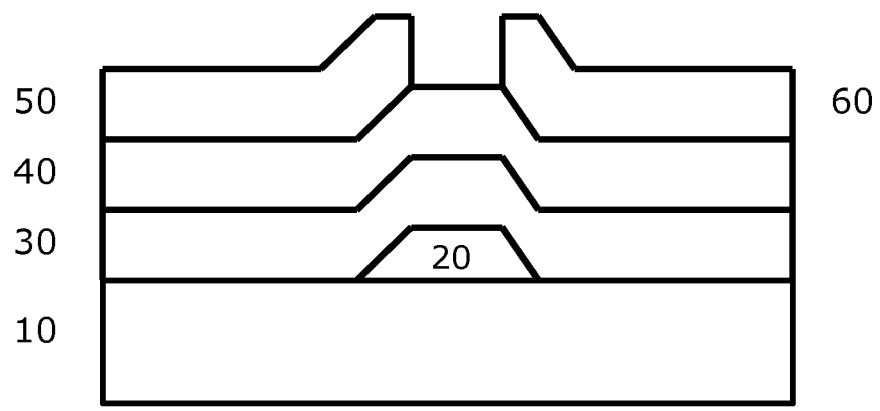
FIG. 2 shows an embodiment of a thin film transistor. A thin film transistor can include a substrate 10, a gate electrode 20, a gate insulation layer 30, an oxide semiconductor layer 40, a source electrode 50, and a drain electrode 60.

Referring to FIG. 2, a thin film transistor of this invention can include a substrate 10, a gate electrode 20, a gate insulation layer 30, an oxide semiconductor layer 40, a source electrode 50, a drain electrode 60, one or more passivation layers, and a protective layer.

A conducting oxide material is useful as an electrode material for gate electrodes 20, source electrodes 50 or drain electrodes 60.

In some aspects, the thickness of an electrode material layer may be from about 100 to about 1000 nanometers.

The gate insulation layer 30 can be deposited on the gate electrode 20. Examples of a gate insulation layer 30 include aluminum oxide, silicon dioxide, germanium dioxide, silicon nitride, germanium nitride, and mixtures thereof.

In some embodiments, molecular precursor compounds and ink compositions of this invention can be used to make IGZO materials useful as an oxide semiconducting layer 40.

In some aspects, the thickness of an oxide semiconducting layer 40 may be from about 10 to about 200 nanometers.

Examples of a substrate 10 include metal, glass and plastic.

One or more passivation layers can be used to cover the source electrode, oxide semiconductor layer, and drain electrode. Examples of a passivation layer include silicon dioxide, germanium dioxide, silicon nitride, and germanium nitride.

Ink Compositions

Embodiments of this disclosure provide isolated molecular precursor compounds that have surprisingly high solubility in an ink composition. Ink compositions of this disclosure may therefore provide a high throughput process for depositing precursors for making IGZO materials, as well as devices including TFTs and TTFTs.

The isolated molecular precursor compounds can be in solid or liquid form.

In some embodiments, a molecular precursor compound may be a viscous liquid or oil. In certain embodiments, a molecular precursor compound that is a viscous liquid may undergo conversion to a material when heated, before volatilization of the compound.

Molecular precursor compounds and compositions of this invention having controlled stoichiometry can be dissolved to make inks. In certain aspects, this disclosure provides precursor compounds that are surprisingly soluble in an organic solvent or a mixture of organic solvents.

The precursor compounds that are solubilized in an ink composition of this disclosure may be synthesized to have the stoichiometry of a desired IGZO material.

In some embodiments, precursor compounds can be solubilized in an ink composition by mixing the precursor compounds with one or more organic solvents.

In some embodiments, an ink composition may be formed by dissolving precursor compounds in a solvent or solvent mixture.

The concentration of a component in an ink composition of this disclosure may be from 0.01% to 99% (v/v), or from 1% to 99% (v/v), or from 1% to 50% (v/v), or from 1% to 30% (v/v), or from 1% to 10% (v/v), or from 1% to 5% (v/v).

The concentration of a component in an ink composition of this disclosure may be from 0.01% to 99% (w/w), or from 1% to 99% (w/w), or from 1% to 50% (w/w), or from 1% to 30% (w/w), or from 1% to 10% (w/w), or from 1% to 5% (w/w).

The concentration of a component in an ink composition of this disclosure may be from 0.01% to 99% (at %), or from 1% to 99% (at %), or from 1% to 50% (at %), or from 1% to 30% (at %), or from 1% to 10% (at %), or from 1% to 5% (at %).

The concentration of a molecular precursor compound in an ink of this disclosure can be from about 0.01% to about 50% (w/w), or from about 0.1% to about 40%, or from about 0.1% to about 25%, or from about 1% to about 15%, or from about 1% to about 5%.

The concentration of a molecular precursor compound in an ink of this disclosure can be from about 1% to about 99% (w/w), or from about 50% to about 99%, or from about 50% to about 75%.

In some embodiments, an ink for making materials requires first providing one or more isolated molecular precursor compounds. The isolated molecular precursor compounds may be used to prepare an ink composition that can be efficiently printed or deposited on a substrate.

This disclosure provides a range of isolated molecular precursor compounds that can be solubilized for preparing an ink composition.

The isolated molecular precursor compounds of this invention can have unexpectedly advantageous solubility and properties for making an ink composition to be printed or deposited on a substrate.

Compositions comprising isolated molecular precursor compounds of this invention can advantageously allow control of the stoichiometry of zinc atoms for making a material.

In further aspects, inks and ink compositions may be made by directly synthesizing molecular precursor compounds in an ink composition.

In some embodiments, molecular precursor compounds for making materials can be prepared in-situ in an ink composition. The ink composition can be efficiently printed or deposited on a substrate.

Ink compositions having one or more molecular precursor compounds prepared in-situ during the ink forming process can advantageously provide a stable ink for efficient, trouble-free use in printing, spraying, coating and other methods.

Ink compositions of this invention having one or more molecular precursor compounds prepared in-situ during the ink forming process can advantageously allow control of the stoichiometry of atoms in an ink composition to be printed or deposited on a substrate.

In some variations, the ink is a solution of the molecular precursors in an organic solvent. The solvent can include one or more organic liquids or solvents. A solvent may be an organic solvent or solvent mixture.

Embodiments of this invention further provide molecular precursor compounds having enhanced solubility in one or more solvents for preparing inks. The solubility of a molecular precursor compound can be selected by variation of the nature and molecular size and weight of one or more organic coordinating species attached to the compound.

Examples of a solvent for an ink of this disclosure include H(OROR), and HOR, where —OROR and —OR are as described above.

Examples of a solvent for an ink of this disclosure include alcohol, methanol, ethanol, isopropyl alcohol, sec-butanol, thiols, butanol, butanediol, glycerols, alkoxyalcohols, glycols, 1-methoxy-2-propanol, acetone, ethylene glycol, propylene glycol, propylene glycol laurate, ethylene glycol ethers, diethylene glycol, triethylene glycol monobutylether, propylene glycol monomethylether, 1,2-hexanediol, ethers, diethyl ether, aliphatic hydrocarbons, aromatic hydrocarbons, dodecane, hexadecane, pentane, hexane, heptane, octane, isooctane, decane, cyclohexane, p-xylene, m-xylene, o-xylene, benzene, toluene, xylene, tetrahydrofuran, 2-methyltetrahydrofuran, siloxanes, cyclosiloxanes, silicone fluids, halogenated hydrocarbons, dibromomethane, dichloromethane, dichloroethane, trichloroethane chloroform, methylene chloride, acetonitrile, esters, acetates, ethyl acetate, butyl acetate, acrylates, isobornyl acrylate, 1,6-hexanediol diacrylate, polyethylene glycol diacrylate, ketones, acetone, methyl ethyl ketone, cyclohexanone, butyl carbitol, cyclopentanone, lactams, N-methyl pyrrolidone, N-(2-hydroxyethyl)-pyrrolidone, cyclic acetals, cyclic ketals, aldehydes, amines, diamines, amides, dimethylformamide, methyl lactate, oils, natural oils, terpenes, and mixtures thereof.

An ink of this disclosure may further include components such as a thickener or a viscosity modifier. Each of these components may be used in an ink of this disclosure at a level of from about 0.001% to about 10% (v/v) or more of the ink composition.

The viscosity of an ink of this disclosure can be from about 0.5 centipoise (cP) to about 10,000 cP.

The viscosity of an ink of this disclosure can be from about 0.5 centipoise (cP) to about 1,000 cP.

The viscosity of an ink of this disclosure can be from about 0.5 centipoise (cP) to about 100 cP.

The viscosity of an ink of this disclosure can be from about 0.5 centipoise (cP) to about 10 cP.

An ink composition of this invention may contain any of the dopant elements disclosed herein, or a dopant known in the art.

Ink compositions of this disclosure can be made by methods known in the art, as well as methods disclosed herein.

Processes for IGZO Materials

In further aspects, processes for making a IGZO material for a thin film transistor can include a step of converting a molecular precursor compound, or an ink or a composition thereof, into a IGZO material.

As used herein, converting refers to a process, for example a heating or thermal process, which converts a molecular precursor compound, which may be a solid, or a liquid, or may be dissolved in a solution, an ink, or an ink composition, into a material. For example, the material may be a IGZO material.

In certain embodiments, one or more molecular precursor compounds can be solubilized in an ink composition and deposited as an image on a substrate. The molecular precursor compounds may be converted to form a material. A thin film transistor can be fabricated in part from the thin film material.

In certain embodiments, one or more molecular precursor compounds can be prepared and solubilized in-situ to form an ink composition. The ink composition can be printed or deposited as a molecular film image on a substrate and optionally dried in a drying stage. The molecular precursor compounds in the film can be further converted to form a material. A thin film transistor can be fabricated in part from the material.

In certain embodiments, one or more molecular precursor compounds can be utilized in liquid form. The molecular precursor compounds may be converted to form a material. A thin film transistor can be fabricated in part from the thin film material.

A patterned layer or image on a substrate can be composed of multiple layers and/or images of an ink. In some embodiments, an image or layer may be converted to a material before, during or after the depositing or printing of an additional image or layer.

The step of converting a molecular precursor compound into a material can be performed by thermal treatment. In some embodiments, a molecular precursor compound can be converted by the application of heat, light, or other energy, or for example, UV light or microwave irradiation.

A step of converting a molecular precursor compound into a material can be performed by thermal treatment.

The step of converting a molecular precursor compound into a material can be performed by heating to temperatures below about 500° C., below about 400° C., or below about 300° C., or below about 200° C.

The step of converting a molecular precursor compound into a material can be performed at various temperatures including from about 50° C. to about 500° C., or from about 100° C. to about 500° C., or from about 150° C. to about 300° C., or from about 150° C. to about 350° C., or from about 200° C. to about 300° C.

In some embodiments, a step of converting a molecular precursor compound in a deposited ink into a thin film material can be done in ambient air, or dry air, or air with controlled humidity.

In some embodiments, a step of converting a molecular precursor compound in a deposited ink into a thin film material can be done in an inert atmosphere or under vacuum.

The step of converting a molecular precursor compound into a material can be performed for times ranging from 10 seconds to 60 minutes, or from 10 seconds to 30 minutes, or from 30 seconds to 10 minutes.

In certain embodiments, a step of converting a molecular precursor compound in a deposited ink into a thin film material can be done in an inert atmosphere after exposure of the wet or dried molecule film to ambient air, or dry air, or air with controlled humidity.

In certain aspects, a step of converting a molecular precursor compound in a deposited ink into a thin film material can be done under reducing conditions or with exposure to a reducing atmosphere. Examples of a reducing atmosphere include 1% $H_2$/99% $N_2$, and 5% $H_2$/95% $N_2$.

In certain aspects, a step of converting a molecular precursor compound in a deposited ink into a thin film material can be done under oxidizing conditions or with exposure to an oxidizing atmosphere. Examples of an oxidizing atmosphere include 1% $O_2$/99% $N_2$, 10% $O_2$/90% $N_2$, and air.

Molecular precursor compounds in a printed or deposited ink on a substrate can be converted to a material by applying energy to the substrate or to the deposited film on the substrate.

Molecular precursor compounds in a deposited layer may be converted to a material before, during or after the deposition of a different layer.

In further aspects, a thin film transistor can be fabricated in part by depositing solid layers of a IGZO material of this disclosure.

Layers can be made by printing, spraying, coating or other methods involving solutions or inks. Aspects of this invention can provide compounds and compositions to provide continuous transport of a solution or ink through an outlet, slot, die or print head. For example, inkjet printing can be performed with high throughput. Printing methods can be enhanced by using molecular precursor compounds of this invention that are soluble components of the ink.

In general, this invention can provide stable ink forms which lack particulates and are suitable for efficient printing, spraying, or coating to make materials.

As used herein, a component can be a compound, an element, a material, or a composition.

Processes for Printing and Depositing Molecular Precursors

The molecular precursors of this invention can be used to make materials by printing or depositing a layer onto a substrate. The deposited layer may be a film or a thin film.

As used herein, the terms "deposit," "depositing," and "deposition" refer to any method for placing a compound or composition onto a surface or substrate, including spraying, coating, and printing.

The molecular precursors of this invention, and inks and compositions made from molecular precursors, can be deposited onto a substrate using methods known in the art, as well as methods disclosed herein.

Examples of methods for depositing a molecular precursor onto a surface or substrate include all forms of printing, spraying, and coating.

Examples of methods for printing using an ink of this disclosure include printing, inkjet printing, aerosol jet printing, gravure printing, reverse gravure printing, reverse offset gravure printing, stamp printing, transfer printing, pad printing, spray pattern printing, flexographic printing, contact printing, reverse printing, thermal printing, lithography, electrophotographic printing, screen printing, and combinations thereof.

Examples of methods for depositing a molecular precursor onto a surface or substrate include spraying, spray coating, spray deposition, and spray pyrolysis.

Examples of methods for depositing a molecular precursor onto a surface or substrate include coating, dip coating, wet coating, spin coating, knife coating, roller coating, rod coating, slot die coating, meyerbar coating, lip direct coating, capillary coating, liquid deposition, solution deposition, layer-by-layer deposition, spin casting, and solution casting.

Examples of methods for printing molecular precursor inks of this invention include direct pattern printing.

Examples of methods for printing or depositing molecular precursor inks of this invention include area printing followed by etching.

In some embodiments, etching can be done by chemical methods or dry etching.

In certain embodiments, because of the advantageous solubility of the molecular precursor compounds of this invention, etching can be done by solvent-based washing or wet etching of a deposited molecular precursor ink or film. This etching can be done by a solvent-wetted pad, solvent-wetted mask, or solvent-wetted template.

Etching can be done after ink deposition, either before or after drying, or after molecule conversion. Etching can be done after a subsequent thermal treatment.

The molecular precursors of this invention, and ink compositions made from molecular precursors, can be deposited onto a substrate using methods known in the art, as well as methods disclosed herein.

In some embodiments, direct pattern printing can be used to circumvent the need for etching steps. Direct pattern printing using inks of this disclosure can be performed without the need for a separate etching step. A pattern of ink may be directly printed using various printing methods to provide a patterned film of a molecular precursor compound on a substrate. The molecular precursor compound in the resulting patterned film can then be converted to form a patterned thin film IGZO material with controlled thickness and composition. The patterned thin film material can be used for TFT/TTFT fabrication and other applications.

In some embodiments, a process for printing can be performed in a single pass to provide a thickness of a thin film material of from 10 to 500 nanometers.

In some embodiments, a process for coating can be performed in a single pass to provide a thickness of a thin film material of from 10 to 500 nanometers.

In some embodiments, a process for spraying can be performed in one second to provide a thickness of a thin film material of from 10 to 5000 nanometers.

In certain embodiments, a first molecular precursor may be deposited onto a substrate, and subsequently a second molecular precursor may be deposited onto the substrate. In certain embodiments, several different molecular precursors may be deposited onto the substrate to create a layer.

In certain variations, different molecular precursors may be deposited onto a substrate simultaneously, or sequentially, whether by spraying, coating, printing, or by other methods. The different molecular precursors may be contacted or mixed before the depositing step, during the depositing step, or after the depositing step. The molecular precursors can be contacted before, during, or after the step of transporting the molecular precursors to the substrate surface.

The depositing of molecular precursors, including by spraying, coating, and printing, can be done with exposure to ambient air, or dry air, or air with controlled humidity, as well as in a controlled or inert atmosphere, such as in dry nitrogen and other inert gas atmospheres, as well as in a partial vacuum atmosphere.

Processes for printing, depositing, spraying, or coating molecular precursors can be done at various temperatures including from about 0° C. to about 100° C., or from about 20° C. to about 70° C.

Transforming Films or Images

Processes for making a material can include a step of transforming or converting a molecular precursor compound into a material.

The step of converting a molecular precursor compound into a material can be performed by thermal treatment. In some embodiments, a molecular precursor compound can be converted by the application of heat, light, or other energy, or for example, UV light or microwave irradiation.

The step of converting a molecular precursor compound into a material can be performed by heating to temperatures below about 500° C., below about 400° C., or below about 300° C., or below about 200° C.

The step of converting a molecular precursor compound into a material can be performed at various temperatures including from about 50° C. to about 500° C., or from 100° C. to about 500° C., or from about 150° C. to about 300° C., or from about 150° C. to about 350° C., or from about 200° C. to about 300° C.

In some embodiments, a step of converting a molecular precursor compound in a deposited ink into a thin film material can be done in ambient air, or dry air, or air with controlled humidity.

In some embodiments, a step of converting a molecular precursor compound in a deposited ink into a thin film material can be done in an inert atmosphere.

In certain embodiments, a step of converting a molecular precursor compound in a deposited ink into a thin film material can be done in an inert atmosphere after exposure of the wet or dried molecule film to ambient air, or dry air, or air with controlled humidity.

In certain aspects, a step of converting a molecular precursor compound in a deposited ink into a thin film material can be done under reducing conditions or with exposure to a reducing atmosphere. Examples of a reducing atmosphere include 1% $H_2$/99% $N_2$, and 5% $H_2$/95% $N_2$.

In certain aspects, a step of converting a molecular precursor compound in a deposited ink into a thin film material can be done under oxidizing conditions or with exposure to an oxidizing atmosphere. Examples of an oxidizing atmosphere include 1% $O_2$/99% $N_2$, 10% $O_2$/90% $N_2$, and air.

The step of converting a molecular precursor compound into a material can be performed for times ranging from 10 seconds to 60 minutes, or from 10 seconds to 30 minutes, or from 30 seconds to 10 minutes.

In certain aspects, depositing of molecular precursors on a substrate can be done while the substrate is heated. In these variations, a material may be deposited or formed directly on the substrate.

In some variations, a substrate can be cooled after a step of heating. In certain embodiments, a substrate can be cooled before, during, or after a step of depositing a molecular precursor or ink thereof.

Embodiments of this disclosure further contemplate articles made by depositing a layer or image onto a substrate, where the layer or image comprises one or more molecular precursor compounds. The article may be a substrate having a layer of a film, or a thin film, or an image which is printed, deposited, sprayed, or coated onto the substrate.

In certain variations, an article may have a substrate printed with a molecular precursor ink, where the ink is printed in an image pattern on the substrate.

Post-Deposition Treatment

In some embodiments, a product material can be further treated post-deposition for material activation. A material can be activated by heating at a temperature of from about 50° C. to about 500° C., or from 100° C. to about 500° C., or from about 150° C. to about 300° C., or from about 150° C. to about 350° C., or from about 200° C. to about 300° C.

Post-deposition treatment for material activation can be done immediately after conversion of a layer to a material, or after any step in the fabrication process of a device.

In some embodiments, a product material can be further treated to increase its crystallinity, or to transform an amorphous material into a crystalline or semicrystalline material. A material can be further treated by heating at a temperature of from about 50° C. to about 500° C., or from 100° C. to about 500° C., or from about 150° C. to about 300° C., or from about 150° C. to about 350° C., or from about 200° C. to about 300° C.

A step of post-deposition treatment can be performed for times ranging from 5 minutes to 200 minutes, or from 10 minutes to 100 minutes.

Further treatment of a material can be done after conversion of a layer to a material, or after any step in the fabrication process of a thin film transistor.

Post-deposition treatment can be performed in ambient air, or dry air, or air with controlled humidity.

In some embodiments, post-deposition treatment can be performed in an inert atmosphere, or under vacuum.

In some embodiments, post-deposition treatment can be performed under reduced atmospheric pressure, or in a vacuum or evacuated vessel.

In certain embodiments, post-deposition treatment can be performed in an inert atmosphere after exposure of the wet or dried molecule film to ambient air, or dry air, or air with controlled humidity.

In certain aspects, post-deposition treatment can be performed under reducing conditions or with exposure to a reducing atmosphere. Examples of a reducing atmosphere include 1% $H_2$/99% $N_2$, and 5% $H_2$/95% $N_2$.

In certain aspects, post-deposition treatment can be performed under oxidizing conditions or with exposure to an oxidizing atmosphere. Examples of an oxidizing atmosphere include 1% $O_2$/99% $N_2$, 10% $O_2$/90% $N_2$, and air.

Substrates

Examples of substrates on which a molecular precursor of this disclosure can be deposited or printed include glass, ceramics, metals, polymers, plastics, and combinations thereof.

Examples of substrates include polymers, plastics, conductive polymers, copolymers, polymer blends, polyethylene terephthalates, polycarbonates, polyesters, polyester films, mylars, polyvinyl fluorides, polyvinylidene fluoride, polyethylenes, polyetherimides, polyethersulfones, polyetherketones, polyimides, polyvinylchlorides, acrylonitrile butadiene styrene polymers, silicones, epoxys, and combinations thereof.

A substrate can be of any thickness or shape.

Structures of Molecular Precursor Compounds Groups

Examples of R alkyl groups include methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl and n-octadecyl.

Examples of R alkyl groups include isopropyl, sec-butyl, isobutyl, tert-butyl, isopentyl, 2-methylbutyl, 3-methylbutyl, 2,2-dimethylbutyl, 2,3-dimethylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,2-dimethylhexyl, 2,3-dimethylhexyl, 2,4-dimethylhexyl, 2,5-dimethylhexyl, 2,2-dimethylpentyl, 3,3-dimethylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, and 3,3-diethylhexyl, and all positional isomers thereof.

Examples of —OR groups include methoxy, ethoxy, n-propoxy, 1-methylethoxy(isopropoxy), butoxy, 1-methylpropoxy(sec-butoxy), 2-methylpropoxy(isobutoxy) or 1,1-dimethylethoxy(tert-butoxy), pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy, heptyloxy, octyloxy, 2-ethylhexyloxy, nonyloxy, decyloxy, and positional isomers thereof.

Examples of R aryl groups include phenyl, naphthyl, anthracenyl, and phenanthrenyl.

In further embodiments, the groups R may independently be (C1-22)alkyl groups. In these embodiments, the alkyl group may be a (C1)alkyl(methyl), or a (C2)alkyl(ethyl), or a (C3)alkyl(propyl), or a (C4)alkyl(butyl), or a (C5)alkyl, or a (C6)alkyl, or a (C7)alkyl, or a (C8)alkyl, or a (C9)alkyl, or a (C10)alkyl, or a (C11)alkyl, or a (C12)alkyl, or a (C13)alkyl, or a (C14)alkyl, or a (C15)alkyl, or a (C16)alkyl, or a (C17)alkyl, or a (C18)alkyl, or a (C19)alkyl, or a (C20)alkyl, or a (C21)alkyl, or a (C22)alkyl.

In certain embodiments, the groups R may independently be (C1-12)alkyl groups. In these embodiments, the alkyl group may be a (C1)alkyl(methyl), or a (C2)alkyl(ethyl), or a (C3)alkyl, or a (C4)alkyl, or a (C5)alkyl, or a (C6)alkyl, or a (C7)alkyl, or a (C8)alkyl, or a (C9)alkyl, or a (C10)alkyl, or a (C11)alkyl, or a (C12)alkyl.

In certain embodiments, the groups R may independently be (C1-6)alkyl groups. In these embodiments, the alkyl group may be a (C1)alkyl(methyl), or a (C2)alkyl(ethyl), or a (C3) alkyl, or a (C4)alkyl, or a (C5)alkyl, or a (C6)alkyl.

Dopants

In some embodiments, an ink made with a molecular precursor compound of this disclosure can include a dopant element. A dopant source compound may be dissolved in an ink composition along with a molecular precursor compound.

A molecular precursor compound or material of this disclosure may contain atoms of one or more dopant elements. Dopant elements include Mg, Y, Ti, Zr, Nb, Cr, Ru, Bi, Sb, La, and mixtures of any of the foregoing.

The quantity of a dopant element in an embodiment of this disclosure can be from about $1 \times 10^{-7}$ atom percent to about 5 atom percent relative to the most abundant metal atom, or greater. In some embodiments, a dopant can be included at a level of from about $1 \times 10^{16}$ $cm^{-3}$ to about $1 \times 10^{21}$ $cm^{-3}$. A dopant can be included at a level of from about 1 ppm to about 10,000 ppm.

In some embodiments, a dopant may include halides including F, Cl and Br which can be supplied from metal haloalkoxides or metal halides. Examples of halide source compounds include $ClIn(OR)_2$, $Cl_2In(OR)$, $ClGa(OR)_2$, $Cl_2Ga(OR)$, $ClAl(OR)_2$, $Cl_2Al(OR)$, $ClB(OR)_2$, $Cl_2B(OR)$, $BrIn(OR)_2$, $Br_2In(OR)$, $BrGa(OR)_2$, $Br_2Ga(OR)$, $BrAl(OR)_2$, $Br_2Al(OR)$, $BrB(OR)_2$, and $Br_2B(OR)$.

In some embodiments, a dopant may include oxides of Mg, Y, Ti, Zr, Nb, Cr, Ru, Bi, Sb, La, and mixtures of any of the foregoing.

Dopant species can be provided from dopant source compounds having the formula $M(OR)_q$, where M is selected from Mg, Y, Ti, Zr, Nb, Cr, Ru, Bi, Sb, La, q is the same as the oxidation state of the atom M, and (OR) is selected from alkoxy, aryloxy, heteroaryloxy, and alkenyloxy.

Examples of dopant source compounds include $Mg(OR)_2$, $Ti(OR)_4$, $Zr(OR)_4$, $Nb(OR)_3$, $Nb(OR)_5$, $Cr(OR)_3$, $Ru(OR)_3$, $La(OR)_3$, and mixtures of any of the foregoing, where the —OR groups are independently selected from alkoxy, aryloxy, heteroaryloxy, and alkenyloxy.

Any of the foregoing dopant source compounds may be used in an ink or ink composition of this invention. A dopant may be introduced into a thin film by any of the deposition methods described herein.

Chemical Definitions

As used herein, the term transition metal refers to atoms of Groups 3 though 12 of the Periodic Table of the elements recommended by the Commission on the Nomenclature of Inorganic Chemistry and published in *IUPAC Nomenclature of Inorganic Chemistry, Recommendations* 2005.

The acronym IGZO refers to a material having the atoms In, Ga, Zn, and O.

With respect to a material, as used herein, the terms atom percent, atom %, or at % refer to the ratio of the number of atoms of an element in a material to the total number of atoms of all elements in the material. For example, in a material that contains atoms of In, Ga, Zn and O, "In at %" means 100 times the number of In atoms divided by the sum of the number of In, Ga, Zn and O atoms. In another example, "0.5 at % X in a material" refers to an amount of X atoms equivalent to 0.5 atom percent of the atoms in the material.

Further, a ratio can be specified in terms of atoms considered, so that in a material that contains atoms of In, Ga, Zn and O, the ratio "In/Ga" means the number of In atoms divided by number of Ga atoms, regardless of the other atoms.

As used herein, the term (X,Y) when referring to compounds or atoms indicates that either X or Y, or a combination thereof may be found in the formula. For example, (In,Ga) indicates that atoms of either In or Ga, or any combination thereof may be found.

The term "alkyl" as used herein refers to a hydrocarbyl radical of a saturated aliphatic group, which can be a branched or unbranched, substituted or unsubstituted aliphatic group containing from 1 to 22 carbon atoms. This definition applies to the alkyl portion of other groups such as, for example, cycloalkyl, alkoxy, alkanoyl, aralkyl, and other groups defined below. The term "cycloalkyl" as used herein refers to a saturated, substituted or unsubstituted cyclic alkyl ring containing from 3 to 12 carbon atoms. As used herein, the term "C(1-5)alkyl" includes C(1)alkyl, C(2)alkyl, C(3)alkyl, C(4)alkyl, and C(5)alkyl. Likewise, the term "C(3-22)alkyl" includes C(1)alkyl, C(2)alkyl, C(3)alkyl, C(4)alkyl, C(5) alkyl, C(6)alkyl, C(7)alkyl, C(8)alkyl, C(9)alkyl, C(10)alkyl, C(11)alkyl, C(12)alkyl, C(13)alkyl, C(14)alkyl, C(15)alkyl, C(16)alkyl, C(17)alkyl, C(18)alkyl, C(19)alkyl, C(20)alkyl, C(21)alkyl, and C(22)alkyl.

As used herein, an alkyl group may be designated by a term such as Me (methyl), Et (ethyl), Pr (any propyl group), "Pr (n-Pr, n-propyl), $^i$Pr (i-Pr, isopropyl), Bu (any butyl group), $^n$Bu (n-Bu, n-butyl), $^i$Bu (i-Bu, isobutyl), $^s$Bu (s-Bu, sec-butyl), and $^t$Bu (t-Bu, tert-butyl).

The term "alkoxy" as used herein refers to an alkyl, cycloalkyl, alkenyl, or alkynyl group covalently bonded to an oxygen atom. The term "alkanoyl" as used herein refers to —C(=O)-alkyl, which may alternatively be referred to as "acyl." The term "alkanoyloxy" as used herein refers to —O—C(=O)-alkyl groups.

The term "aryl" as used herein refers to any stable monocyclic, bicyclic, or polycyclic carbon ring system of from 4 to 12 atoms in each ring, wherein at least one ring is aromatic. Some examples of an aryl include phenyl, naphthyl, tetrahydro-naphthyl, indanyl, and biphenyl. Where an aryl substituent is bicyclic and one ring is non-aromatic, it is understood that attachment is to the aromatic ring. An aryl may be substituted or unsubstituted.

The term "substituted" as used herein refers to an atom having one or more substitutions or substituents which can be the same or different and may include a hydrogen substituent. Thus, the terms alkyl, cycloalkyl, alkenyl, alkynyl, alkoxy, alkanoyl, alkanoyloxy, alkylamino, alkylaminoalkyl, aryl, heteroaryl, heterocycle, aroyl, and aralkyl as used herein refer to groups which include substituted variations. Substituted variations include linear, branched, and cyclic variations, and groups having a substituent or substituents replacing one or more hydrogens attached to any carbon atom of the group.

It will be understood that "substitution" or "substituted with" refers to such substitution that is in accordance with permitted valence of the substituted atom and the substituent. As used herein, the term "substituted" includes all permissible substituents.

This invention encompasses any and all tautomeric, solvated or unsolvated, hydrated or unhydrated forms, as well as any atom isotope forms of the compounds and compositions disclosed herein.

This invention encompasses any and all crystalline polymorphs or different crystalline forms of the compounds and compositions disclosed herein.

Additional Embodiments

All publications, references, patents, patent publications and patent applications cited herein are each hereby specifically incorporated by reference in their entirety for all purposes.

While this invention has been described in relation to certain embodiments, aspects, or variations, and many details have been set forth for purposes of illustration, it will be apparent to those skilled in the art that this invention includes additional embodiments, aspects, or variations, and that some of the details described herein may be varied considerably without departing from this invention. This invention includes such additional embodiments, aspects, and variations, and any modifications and equivalents thereof. In particular, this invention includes any combination of the features, terms, or elements of the various illustrative components and examples.

The use herein of the terms "a," "an," "the" and similar terms in describing the invention, and in the claims, are to be construed to include both the singular and the plural.

The terms "comprising," "having," "include," "including" and "containing" are to be construed as open-ended terms which mean, for example, "including, but not limited to." Thus, terms such as "comprising," "having," "include," "including" and "containing" are to be construed as being inclusive, not exclusive.

Recitation of a range of values herein refers individually to each and any separate value falling within the range as if it were individually recited herein, whether or not some of the values within the range are expressly recited. For example, the range "4 to 12" includes without limitation any whole, integer, fractional, or rational value greater than or equal to 4 and less than or equal to 12, as would be understood by those skilled in the art. Specific values employed herein will be understood as exemplary and not to limit the scope of the invention.

Recitation of a range of a number of atoms herein refers individually to each and any separate value falling within the range as if it were individually recited herein, whether or not some of the values within the range are expressly recited. For example, the term "C1-8" includes without limitation the species C1, C2, C3, C4, C5, C6, C7, and C8.

The examples given herein, and the exemplary language used herein are solely for the purpose of illustration, and are not intended to limit the scope of the invention. All examples and lists of examples are understood to be non-limiting.

When a list of examples is given, such as a list of compounds, molecules or compositions suitable for this invention, it will be apparent to those skilled in the art that mixtures of the listed compounds, molecules or compositions may also be suitable.

EXAMPLES

All manipulations were performed under inert atmosphere using Schlenk techniques or in an inert atmosphere glove box, unless otherwise specified. Alcohols were distilled from Na metal and stored over activated 4 Å molecular sieves. 70% $HNO_3$ was purchased from Aldrich and used as received.

Example 1

IGZO Molecular Precursor Compound InGaZn $(OCH_2CH_2OCH(CH_3)_2)_8$

To a magnetically stirring mixture of $[Zn(OCH_2CH_2OCH(CH_3)_2)_2]_n$ (1.02 g, 3.74 mmol), $Ga[OCH_2CH_2OCH(CH_3)_2]_3$ (1.40 g, 3.70 mmol) and $In[OCH_2CH_2OCH(CH_3)_2]_3$ (1.61 g, 3.78 mmol) in toluene (40 mL) at 23° C. (room temperature) was added $HOCH_2CH_2OCH(CH_3)_2$ (7.0 mL, 61 mmol) via syringe over ~5 min. The reaction mixture was heated at 60° C. (oil bath) for 5 h with continuous stirring, resulting in formation of a colorless solution. The volatile species were then removed at 23° C. (room temperature) under reduced pressure. The resulting residue was heated at 50° C. under reduced pressure for 2 h and isolated to afford a colorless solid (4.0 g, yield 99%).

$^1$H: δ (400 MHz, $C_6D_6$): 4.6-3.5 (m, 40H), 1.6-1.0 (m, 48H). δ (400 MHz, $CDCl_3$): 4.18-3.78 (broad m, 16H), 3.72-3.38 (broad m, 24H), 1.22-1.02 (broad m, 48H).

Elemental analysis: Found, C, 44.4; H, 8.1; In, 10.3%; Ga, 6.2%; Zn, 6.1%; Theoretical, C, 45.0; H, 8.3; In, 10.8%; Ga, 6.5%; Zn, 6.1%. From these data the following ratios for the compound were determined: Found=0.97:0.96:1.0. Theoretical In/Ga/Zn=1.0:1.0:1.0.

The TGA for conversion of this molecular precursor compound to a material showed a transition beginning at about 210° C., having a midpoint at about 243° C., and ending at about 280° C. The ceramic yield for the transition was 29.8%, as compared to a theoretical yield for the formula $InGaZnO_4$ of 29.2%. Thus, the TGA showed that this molecular precursor can be used to prepare IGZO layers and materials, and can be used as a component to prepare transistors and devices.

Example 2

IGZO Molecular Precursor Compound $Ga_{0.95}In_{1.9}Zn[OCHCH_3CH_2OC(CH_3)_3]_{8.55}[OCH_2CH_2OCH(CH_3)_2]_2$ A mixture of $Zn[OCH_2CH_2OCH(CH_3)_2]_2$ (0.163 g, 0.600 mmol), $Ga[OCHCH_3CH_2OC(CH_3)_3]_3$ (0.262 g, 0.565 mmol), $In[OCHCH_3CH_2OC(CH_3)_3]_3$ (0.575 g, 1.13 mmol), and toluene (50 mL) was heated at 70° C. with stirring. After 2 h of heated stirring, the reaction mixture changed from a cloudy suspension to a clear and colorless solution. The reaction mixture was then cooled to 23° C. (room temperature) and filtered through a glass fiber pad. The volatile components were removed under reduced pressure and the resulting residue was heated under reduced pressure at 60° C. for 1 h to afford a colorless oil, which was further dried to afford a colorless solid (0.74 g, 74%).

$^1$H (400 MHz, $C_6D_6$): 4.43-3.79 (broad m, 11.5H), 3.76-2.83 (broad m, 23.1H), 1.74-0.97 (broad m, 114.6H).

ICP elemental analysis: Found In/Ga/Zn=1.99:0.95:1.0. Theoretical In/Ga/Zn=1.90:0.95:1.0.

The TGA for conversion of this molecular precursor compound to a material showed a transition beginning at about 170° C., having a midpoint at about 211° C., and ending at about 250° C. The ceramic yield was 29.6%, as compared to a theoretical yield for the formula $In_{1.9}Ga_{0.95}ZnO_{5.275}$ of 29.6%. Thus, the TGA showed that this molecular precursor can be used to prepare IGZO layers and materials, and can be used as a component to prepare transistors and devices.

Example 3

IGZO Molecular Precursor Compound $In_{2.0}Ga_{0.97}Zn(OCH_2CH_2OCH(CH_3)_2)_{10.91}$ To a magnetically stirring mixture of $Zn[OCH_2CH_2OCH(CH_3)_2]_2$ (0.915 g, 3.4 mmol), $Ga[OCH_2CH_2OCH(CH_3)_2]_3$ (1.260 g, 3.3 mmol) and $In[OCH_2CH_2OCH(CH_3)_2]_3$ (2.885 g, 6.8 mmol) in toluene (50 mL) at 23° C. (room temperature) was added $HOCH_2CH_2OCH(CH_3)_2$ (7.0 mL, 6.3 g, 61 mmol) over ~5 min via syringe. The reaction mixture was then heated at 50° C. (oil bath) for 5 h with continuous stirring resulting in a colorless solution. The volatile species were then removed at 23° C. (room temperature) under reduced pressure. The resulting residue was heated at 50° C. under reduced pressure for 2 h and isolated to afford a colorless solid (5.0 g, yield 99%).

$^1$H: δ (400 MHz, $C_6D_6$): 4.6-3.5 (m, 55H), 1.6-1.0 (m, 66H); δ (400 MHz, $CDCl_3$): 4.19-3.79 (m, 22H), 3.70-3.40 (m, 33H), 1.22-1.04 (bs, 66H).

ICP elemental analysis: Found, In, 49.4%; Ga, 24.0%; Zn, 26.7%; Theoretical, In, 50.4%; Ga, 24.4%; Zn, 25.2%. From these data the following ratios for the compound were determined: Found=1.9:0.9:1.0. Theoretical In/Ga/Zn=2.0:0.97:1.0.

The TGA for conversion of this molecular precursor compound to a material showed a transition beginning at about 220° C., having a midpoint at about 240° C., and ending at about 260° C. The ceramic yield for the transition was 31.3%, as compared to a theoretical yield for the formula $In_2Ga_{0.97}ZnO_{5.46}$ of 30.2%. Thus, the TGA showed that this molecular precursor can be used to prepare IGZO layers and materials, and can be used as a component to prepare transistors and devices.

Example 4

IGZO Molecular Precursor Compound $ZnIn_{1.0}Ga_{1.0}[OCH_2CH_2OCH(CH_3)_2]_8$

To a magnetically stirring mixture of $[Zn(OCH_2CH_2OCH(CH_3)_2)_2]_n$ (1.36 g, 5.00 mmol), $Ga[OCH_2CH_2OCH(CH_3)_2]_3$ (1.95 g, 5.14 mmol) and $In[OCH_2CH_2OCH(CH_3)_2]_3$ (2.13 g, 5.02 mmol) in benzene (50 mL) at 23° C. (room temperature) was added $HOCH_2CH_2OCH(CH_3)_2$ (6.0 mL, 52 mmol) via syringe over ~5 min. The reaction mixture was stirred for 16 h at 23° C. (room temperature), resulting in formation of a colorless solution. The volatile species were then removed at 23° C. (room temperature) under reduced pressure. The resulting residue was heated at 60° C. under reduced pressure for 2 h and isolated to afford $ZnIn_{1.0}Ga_{1.0}[OCH_2CH_2OCH(CH_3)_2]_8$ as a colorless solid (4.8 g, 88%).

Example 5

IGZO Molecular Precursor Compound $ZnIn_{2.0}Ga_{1.0}[OCH_2CH_2OCH(CH_3)_2]_{11}$ To a magnetically stirring mixture of $[Zn(OCH_2CH_2OCH(CH_3)_2)_2]_n$ (0.609 g, 2.24 mmol), $Ga[OCH_2CH_2OCH(CH_3)_2]_3$ (0.836 g, 2.20 mmol) and $In[OCH_2CH_2OCH(CH_3)_2]_3$ (1.865 g, 4.40 mmol) in benzene (50 mL) at 23° C. (room temperature) was added $HOCH_2CH_2OCH(CH_3)_2$ (6.0 mL, 52 mmol) via syringe over ~5 min. The reaction mixture was stirred for 12 h at 23° C. (room temperature), resulting in formation of a colorless solution. The volatile species were then removed at 23° C. (room temperature) under reduced pressure. The resulting residue was heated at 60° C. under reduced pressure for 2 h and isolated to afford $\{ZnIn_{2.0}Ga_{1.0}[OCH_2CH_2OCH(CH_3)_2]_{11}\}_n$ as a colorless solid.

Example 6

IGZO Molecular Precursor Compound $In_{1.02}Ga_{1.52}Zn[OCH_2CH_2OCH(CH_3)_2]_{9.62}$ To a magnetically stirring mixture of $In[OCH_2CH_2OCH(CH_3)_2]_3$ (0.925 g, 2.180 mmol), $Ga[OCH_2CH_2OCH(CH_3)_2]_3$ (1.238 g, 3.265 mmol), $Zn[OCH_2CH_2OCH(CH_3)_2]_2$ (0.583 g, 2.146 mmol), and toluene (40 mL) at 23° C. (room temperature) was added $HOCH_2CH_2OCH(CH_3)_2$ (8.0 mL, 7.2 g, 69 mmol) dropwise over 1 min. The resulting colorless solution was subsequently stirred at 23° C. for 16 h, followed by removal of the volatile species under reduced pressure at 23° C. and heating of the residue under reduced pressure at 80° C. for 2 h to afford the product as a pale yellow oil (2.40 g, 87%).

$^1$H ($CDCl_3$, 400 MHz): 4.41-4.29 (m, 1.09H), 4.15-3.20 (m, 49.1H), 1.34-0.89 (m, 57.72H).

ICP elemental analysis: Found In/Ga/Zn=1.03:1.51:1.0. Theoretical In/Ga/Zn=1.02:1.52:1.0.

Example 7

IGZO Molecular Precursor Compound $ZnIn_{2.0}Ga_{1.0}[OCH_2CH_2OCH(CH_3)_2]_{11}$ To a magnetically stirring mixture of $[Zn(OCH_2CH_2OCH(CH_3)_2)_2]_n$ (0.602 g, 2.22 mmol), $Ga[OCH_2CH_2OCH(CH_3)_2]_3$ (0.842 g, 2.22 mmol) and $In[OCH_2CH_2OCH(CH_3)_2]_3$ (1.893 g, 4.46 mmol) in benzene (50 mL) at 23° C. (room temperature) was added $HOCH_2CH_2OCH(CH_3)_2$ (15.0 mL, 130 mmol) via syringe over ~5 min. The reaction mixture was stirred for 2 h at 23° C. (room temperature), resulting in formation of a colorless solution. The volatile species were then removed at 23° C. (room temperature) under reduced pressure. The resulting residue was heated at 100° C. under reduced pressure for 4 h and isolated to afford {ZnIn$_{2.0}$Ga$_{1.0}$[OCH$_2$CH$_2$OCH(CH$_3$)$_2$]$_{11}$}$_n$ as a colorless solid.

Example 8

IGZO Molecular Precursor Compound InGaZn(OCH$_2$CH$_2$OCH(CH$_3$)$_2$)$_8$

Figure 3:
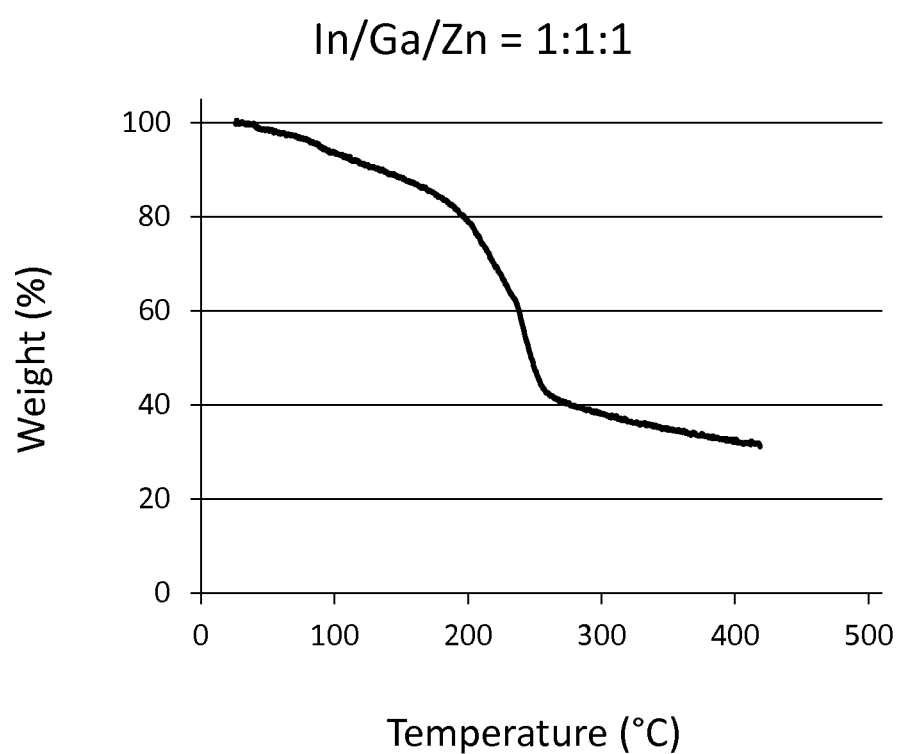
FIG. 3 shows the TGA trace for conversion of molecular precursor compound $InGaZn(OCH_2CH_2OCH(CH_3)_2)_8$ into an IGZO material having an In/Ga/Zn stoichiometry of 1:1:1. The TGA trace shows that this molecular precursor compound can be used to prepare IGZO layers and materials with targeted stoichiometry.

FIG. 3 shows the TGA trace for conversion of InGaZn(OCH$_2$CH$_2$OCH(CH$_3$)$_2$)$_8$ which had a transition beginning at about 210° C. and ending at about 265° C. The ceramic yield for the transition was 30%, as compared to a theoretical yield for the formula InGaZnO$_4$ of 30%. Thus, the TGA trace shows that this molecular precursor can be used to prepare IGZO layers and materials.

Example 9

Figure 4:
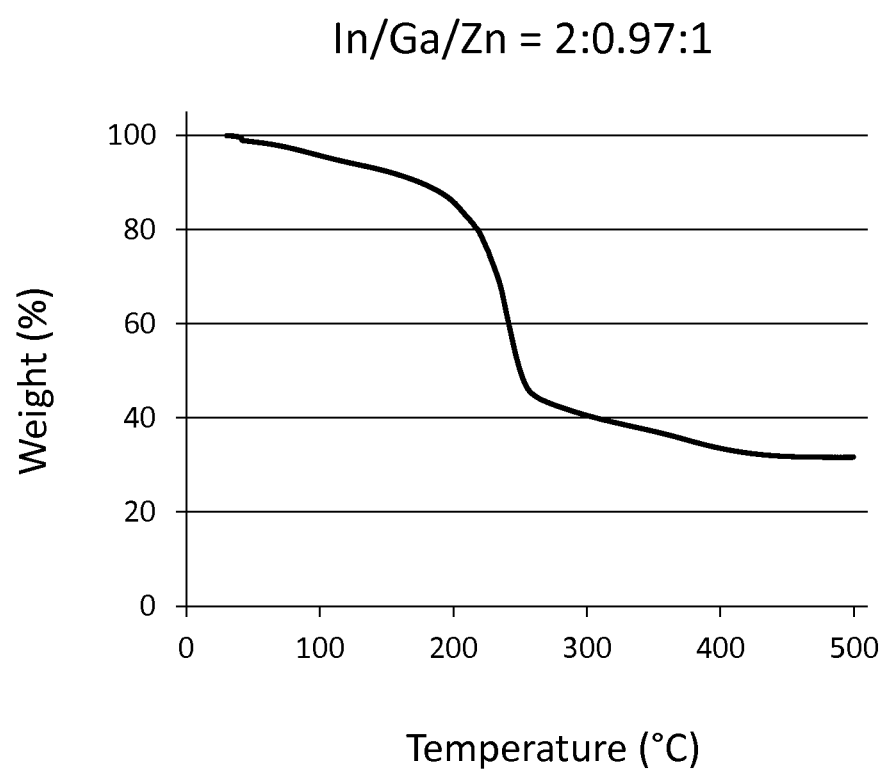
FIG. 4 shows the TGA trace for conversion of molecular precursor compound $In_2GaZn(OCH_2CH_2OCH(CH_3)_2)_{11}$ into an IGZO material having an In/Ga/Zn stoichiometry of 2:1:1. The TGA trace shows that this molecular precursor compound can be used to prepare IGZO layers and materials with targeted stoichiometry.

IGZO Molecular Precursor Compound In$_2$GaZn(OCH$_2$CH$_2$OCH(CH$_3$)$_2$)$_{11}$ FIG. 4 shows the TGA trace for conversion of In$_2$GaZn(OCH$_2$CH$_2$OCH(CH$_3$)$_2$)$_{11}$ which had a transition beginning at about 200° C. and ending at about 260° C. The ceramic yield for the transition was 31%, as compared to a theoretical yield for the formula In$_2$GaZnO$_4$ of 31%. Thus, the TGA trace shows that this precursor can be used to prepare IGZO layers and materials.

Example 10

IGZO Molecular Precursor Compound In$_{3.05}$Ga$_{0.99}$Zn[OCH$_2$CH$_2$OCH(CH$_3$)$_2$]$_{14.12}$ To a magnetically stirring mixture of In[OCH$_2$CH$_2$OCH(CH$_3$)$_2$]$_3$ (1.086 g, 2.560 mmol), Ga[OCH$_2$CH$_2$OCH(CH$_3$)$_2$]$_3$ (0.314 g, 0.827 mmol), Zn[OCH$_2$CH$_2$OCH(CH$_3$)$_2$]$_2$ (0.228 g, 0.839 mmol), and toluene (40 mL) at 23° C. (room temperature) was added HOCH$_2$CH$_2$OCH(CH$_3$)$_2$ (2.0 mL, 1.8 g, 17 mmol) dropwise over 1 min. The resulting mixture was stirred at 50° C. for 16 h, resulting in formation of a colorless solution. Filtration through a glass fiber filter pad at 23° C. followed by removal of the volatile species under reduced pressure at 23° C. and heating of the residue under reduced pressure at 80° C. for 2 h afforded the product as a colorless solid (1.40 g, 86%).
$^1$H (CDCl$_3$, 400 MHz): 4.21-3.80 (broad m, 24.2H), 3.79-3.69 (broad m, 6.1H), 3.68-3.45 (m, 36.3H), 2.60-2.47 (m, 2.1H), 1.36-0.99 (broad m, 84.7H).
ICP elemental analysis: Found In/Ga/Zn=2.98:1.07:1.00. Theoretical In/Ga/Zn=3.05:0.99:1.00.
The TGA for conversion of this molecular precursor compound to a material showed a transition beginning at about 190° C., having a midpoint at about 233° C., and ending at about 346° C. The ceramic yield for the transition was 32.3%, as compared to a theoretical yield for the formula In$_{3.05}$Ga$_{0.99}$ZnO$_{7.06}$ of 30.8%. Thus, the TGA showed that this molecular precursor can be used to prepare IGZO layers and materials, and can be used as a component to prepare transistors and devices.

Example 11

IGZO Molecular Precursor Compound In$_{0.75}$Ga$_{0.75}$Zn$_{1.0}$[OCH$_2$CH$_2$OCH(CH$_3$)$_2$]$_{6.44}$ To a magnetically stirring mixture of In[OCH$_2$CH$_2$OCH(CH$_3$)$_2$]$_3$ (1.192 g, 2.810 mmol), Ga[OCH$_2$CH$_2$OCH(CH$_3$)$_2$]$_3$ (1.059 g, 2.793 mmol), Zn[OCH$_2$CH$_2$OCH(CH$_3$)$_2$]$_2$ (1.015 g, 3.736 mmol), and toluene (40 mL) at 23° C. (room temperature) was added HOCH$_2$CH$_2$OCH(CH$_3$)$_2$ (8.0 mL, 7.2 g, 69 mmol) dropwise over 1 min. The resulting colorless solution was subsequently stirred at 23° C. for 16 h, followed by removal of the volatile species under reduced pressure at 23° C. and heating of the residue under reduced pressure at 80° C. for 2 h to afford the product as a colorless solid (2.80 g, 86%).
$^1$H (CDCl$_3$, 400 MHz): 4.21-3.80 (broad m, 13H), 3.72-3.40 (broad m, 19.5H), 1.38-1.11 (broad m, 39H).
ICP elemental analysis: Found In/Ga/Zn=0.74:0.74:1.0. Theoretical In/Ga/Zn=0.75:0.75:1.

Example 12

Monomer Compound Zn[OCH$_2$CH$_2$OCH(CH$_3$)$_2$]$_2$

To neat HOCH$_2$CH$_2$OCH(CH$_3$)$_2$ (13.0 mL, 11.8 g, 113 mmol) at 0° C. (ice bath) in a 200 mL reaction flask was added diethylzinc (1M in hexane, 50.0 mL, 50.0 mmol) slowly (over ~10 min) via cannula transfer. The reaction was exothermic and gas evolution was observed. Upon completion of the ZnEt$_2$ addition and stirring for an additional ~30 min, a colorless precipitate was observed. The reaction mixture was then stirred at 23° C. (room temperature) for 18 h. The liquid was decanted and the precipitate was heated at 100° C. under dynamic vacuum for 2 h to remove the remaining volatile species leaving behind 11.50 g of a colorless powder (85% yield).
Elemental analysis: Found, C, 44.2; H, 8.7; Zn, 22.7%; Theoretical, C, 44.2; H, 7.4; Zn, 24.1%.

Example 13

Monomer Compound In[OCH$_2$CH$_2$OCH(CH$_3$)$_2$]$_3$

To a magnetically stirring suspension of In[N(SiMe$_3$)$_2$]$_3$ (9.34 g, 15.7 mmol) in toluene (200 mL) at 23° C. (room temperature) in a 1 L flask was added HOCH$_2$CH$_2$OCH(CH$_3$)$_2$ (5.4 mL, 4.9 g, 47 mmol) as a neat liquid over ~5 min via syringe. The clear and colorless reaction mixture was then heated in an oil bath at 70° C. for 18 h with stirring, followed by removal of the volatile species under reduced pressure at 23° C. (room temperature) leaving behind a colorless solid. The solid residue was subsequently heated at 50° C. under reduced pressure for 2 h. Solid {In[OCH$_2$CH$_2$OCH(CH$_3$)$_2$]$_3$}$_n$ was isolated and stored under inert atmosphere (5.6 g, 85% yield).
$^1$H: δ (C$_6$D$_6$, 400 MHz) 4.4-3.4 (m, 12H), 1.33 (m, 9H), 0.95-0.90 (m, 9H); δ (CDCl$_3$, 400 MHz) 4.04 (broad s, 6H), 3.58 (broad s, 9H), 1.11 (broad s, 18H).
Elemental analysis: Found, C, 41.8; H, 7.7; In, 25.8%; Theoretical, C, 42.5; H, 7.1; In, 27.1%.

Example 14

Monomer Compound In(OCHCH$_3$CH$_2$OC(CH$_3$)$_3$)$_3$

To a magnetically stirring mixture of In[N(SiMe$_3$)$_2$]$_3$ (4.37 g, 7.33 mmol) and toluene (50 mL) at 23° C. (room temperature) was added HOCHCH$_3$CH$_2$OC(CH$_3$)$_3$ (3.3 mL, 2.9 g, 21.8 mmol) dropwise over 5 min followed by stirring an additional 10 min at 23° C. The reaction mixture was subsequently stirred at 60° C. (oil bath) for 18 h. The reaction mixture was then cooled to 23° C. and filtered through a glass fiber pad. The volatile species were removed from the filtrate under reduced pressure at 23° C. followed by heating of the residue under reduced pressure at 60° C. for 1 h to afford the product as a colorless oil (3.10 g, 81%).

$^1$H: δ (C$_6$D$_6$, 400 MHz) 4.789-4.042 (broad m, 1H), 3.898-3.085 (broad m, 2H), 1.443-1.110 (broad m, 12H).

Elemental analysis: Found, In, 41.0%; Theoretical, In, 41.3%.

Example 15

Monomer Compound Ga[OCH$_2$CH$_2$OCH(CH$_3$)$_2$]$_3$

To a magnetically stirring colorless solution of Ga(NMe$_2$)$_3$ (4.96 g, 24.6 mmol) in toluene (30 mL) at 23° C. (room temperature) in a 200 mL reaction flask was added HOCH$_2$CH$_2$OCH(CH$_3$)$_2$ (16.7 mL, 15.1 g, 145 mmol) slowly (over ~5 min) via syringe. The reaction was exothermic and gas evolution was observed. Upon completion of the HOCH$_2$CH$_2$OCH(CH$_3$)$_2$ addition, the reaction mixture was heated at 60° C. (oil bath) for 8 h followed by stirring for 18 h at 23° C. (room temperature). The resulting colorless solution was concentrated to dryness under reduced pressure at 23° C. (room temperature) to afford a colorless oil. Subsequent heating at 50° C. under vacuum for 2 h and storage under inert atmosphere for 6 days gave a colorless powder (14.0 g, 76% isolated yield).

$^1$H(C$_6$D$_6$, 400 MHz) δ 4.5-4.4 (m, 12H), 4.4-4.2 (m, 6H), 3.9-3.5 (m, 6H), 1.22 (d $^3J_{HH}$=6 Hz, 9H), 1.18 (d $^3J_{HH}$=5.6 Hz, 9H).

Elemental analysis: Found, C, 48.9; H, 8.7; Ga, 18.8%; Theoretical, C, 47.4; H, 8.0; Ga, 18.4%.

Example 16

Monomer Compound Ga(OCHCH$_3$CH$_2$OC(CH$_3$)$_3$)$_3$

To a magnetically stirring mixture of Ga(NMe$_2$)$_3$ (1.50 g, 7.43 mmol) and toluene (50 mL) at 23° C. (room temperature) was added HOCHCH$_3$CH$_2$OC(CH$_3$)$_3$ (3.4 mL, 3.0 g, 22.5 mmol) dropwise over 5 min followed by stirring an additional 10 min at 23° C. The reaction mixture was subsequently stirred at 60° C. (oil bath) for 18 h. The reaction mixture was then cooled to 23° C. and filtered through a glass fiber pad. The volatile species were removed from the filtrate under reduced pressure at 23° C. followed by heating of the residue under reduced pressure at 60° C. for 1 h to afford the product as a colorless oil (2.80 g, 84%).

$^1$H(C$_6$D$_6$, 400 MHz) δ 4.40 (broad s, 1H), 3.54 (broad s, 1H), 3.30 (broad s, 1H), 1.52 (broad s, 3H), 1.24 (broad s, 9H).

ICP elemental analysis: Found, Ga, 23.0%; Theoretical, Ga, 25.1%.

Example 17

Preparation of Compositionally-Targeted IGZO Thin Films

Inks made from different concentrations of the molecular precursor InGaZn(OCH$_2$CH$_2$OCH(CH$_3$)$_2$)$_8$ were prepared. Each was spin coated onto a substrate leaving a molecular precursor film. The substrate was then heated in air at 300° C. for 5 minutes to form an IGZO thin film.

The compositions of the converted films with respect to the corresponding inks are shown in Table 1.

TABLE 1

Composition of targeted IGZO films
InGaZnO$_4$

| INK | | | CONVERTED FILM | | |
|---|---|---|---|---|---|
| In | Ga | Zn | In | Ga | Zn |
| 1.04 | 1.02 | 1.00 | 0.96 | 0.94 | 1.00 |
| 1.04 | 1.02 | 1.00 | 1.10 | 1.03 | 1.00 |

These results show that the molecular precursor InGaZn(OCH$_2$CH$_2$OCH(CH$_3$)$_2$)$_8$ can be used to make a thin film IGZO material with a controlled stoichiometry and controlled film thickness.

Example 18

Preparation of Compositionally-Targeted IGZO Thin Films

Inks made from different concentrations of the molecular precursor In$_2$GaZn(OCH$_2$CH$_2$OCH(CH$_3$)$_2$)$_{11}$ were prepared. Each was spin coated onto a substrate leaving a molecular precursor film. The substrate was then heated in air at 300° C. for 5 minutes to form an IGZO thin film.

The compositions of converted films with respect to the corresponding inks are shown in Table 2.

TABLE 2

Composition of targeted IGZO films
In$_2$GaZnO$_{5.5}$

| INK | | | CONVERTED FILM | | |
|---|---|---|---|---|---|
| In | Ga | Zn | In | Ga | Zn |
| 1.97 | 1.03 | 1.00 | 1.91 | 1.00 | 1.00 |
| 1.97 | 1.03 | 1.00 | 1.92 | 0.94 | 1.00 |

These results show that the molecular precursor In$_2$GaZn(OCH$_2$CH$_2$OCH(CH$_3$)$_2$)$_{11}$ can be used to make a thin film IGZO material with a controlled stoichiometry and controlled film thickness.

Example 19

IGZO Molecular Precursor Compound Ink Formulations (a) IGZO Ink 1.7%: An ink suitable for formation of an IGZO film with the formula In$_{1.0}$Ga$_{1.0}$ZnO$_{4.0}$ (In/Ga/Zn=1:1:1) was prepared by dissolution of {ZnIn$_{1.0}$Ga$_{1.0}$[OCH$_2$CH$_2$OCH(CH$_3$)$_2$]$_8$}$_n$ (0.098 g, 0.091 mmol) in a mixture of p-xylene (3.367 g) and HOCH$_2$CH$_2$OCH(CH$_3$)$_2$ (2.18 mL, 1.97 g). The resulting colorless solution was composed of 1.7 wt % {ZnIn$_{1.0}$Ga$_{1.0}$[OCH$_2$CH$_2$OCH(CH$_3$)$_2$]$_8$}$_n$.

(b) IGZO Ink 3.6%: An ink suitable for formation of an IGZO film with the formula In$_{1.0}$Ga$_{1.0}$ZnO$_{4.0}$ (In/Ga/Zn=1:1:1) was prepared by dissolution of {ZnIn$_{1.0}$Ga$_{1.0}$[OCH$_2$CH$_2$OCH(CH$_3$)$_2$]$_8$}$_n$ (0.101 g, 0.936 mmol) in a mixture of p-xylene (1.736 g) and HOCH$_2$CH$_2$OCH(CH$_3$)$_2$ (1.03 mL, 0.931 g). The resulting colorless solution was composed of 3.6 wt % $\{ZnIn_{1.0}Ga_{1.0}[OCH_2CH_2OCH(CH_3)_2]_8\}_n$.

(c) IGZO Ink 7.1%: An ink suitable for formation of an IGZO film with the formula $In_{1.0}Ga_{1.0}ZnO_{4.0}$ (In/Ga/Zn=1:1:1) was prepared by dissolution of $\{ZnIn_{1.0}Ga_{1.0}[OCH_2CH_2OCH(CH_3)_2]_8\}_n$ (0.136 g, 0.126 mmol) in a mixture of p-xylene (1.163 g) and $HOCH_2CH_2OCH(CH_3)_2$ (0.692 mL, 0.625 g). The resulting colorless solution was composed of 7.1 wt % $\{ZnIn_{1.0}Ga_{1.0}[OCH_2CH_2OCH(CH_3)_2]_8\}_n$.

(d) IGZO Ink 9.2%: An ink suitable for formation of an IGZO film with the formula $In_{1.0}Ga_{1.0}ZnO_{4.0}$ (In/Ga/Zn=1:1:1) was prepared by dissolution of $\{ZnIn_{1.0}Ga_{1.0}[OCH_2CH_2OCH(CH_3)_2]_8\}_n$ (0.159 g, 0.148 mmol) in a mixture of p-xylene (1.017 g) and $HOCH_2CH_2OCH(CH_3)_2$ (0.61 mL, 0.55 g). The resulting colorless solution was composed of 9.2% wt % $\{ZnIn_{1.0}Ga_{1.0}[OCH_2CH_2OCH(CH_3)_2]_8\}_n$.

(e) IGZO Ink 3.0%: An ink suitable for formation of an IGZO film with the formula $In_{1.0}Ga_{1.0}ZnO_{4.0}$ (In/Ga/Zn=1:1:1) was prepared by dissolution of $\{ZnIn_{1.0}Ga_{1.0}[OCH_2CH_2OCH(CH_3)_2]_8\}_n$ (0.366 g, 0.341 mmol) in a mixture of p-xylene (7.656 g) and $HOCH_2CH_2OCH(CH_3)_2$ (4.56 mL, 4.12 g). The resulting colorless solution was composed of 3.0 wt % $\{ZnIn_{1.0}Ga_{1.0}[OCH_2CH_2OCH(CH_3)_2]_8\}_n$.

(f) IGZO Ink 5.9%: An ink suitable for formation of an IGZO film with the formula $In_{1.0}Ga_{1.0}ZnO_{4.0}$ (In/Ga/Zn=1:1:1) was prepared by dissolution of $\{ZnIn_{1.0}Ga_{1.0}[OCH_2CH_2OCH(CH_3)_2]_8\}_n$ (0.609 g, 0.566 mmol) in a mixture of p-xylene (6.595 g) and $HOCH_2CH_2OCH(CH_3)_2$ (3.55 mL, 3.21 g). The resulting colorless solution was composed of 5.9 wt % $\{ZnIn_{1.0}Ga_{1.0}[OCH_2CH_2OCH(CH_3)_2]_8\}_n$.

(g) IGZO Ink 1.3%: An ink suitable for formation of an IGZO film with the formula $In_{2.0}Ga_{1.0}ZnO_{5.5}$ (In/Ga/Zn=2:1:1) was prepared by dissolution of $\{ZnIn_{2.0}Ga_{1.0}[OCH_2CH_2OCH(CH_3)_2]_{11}\}_n$ (0.044 g, 0.023 mmol) in a mixture of p-xylene (2.867 g) and $HOCH_2CH_2OCH(CH_3)_2$ (0.66 mL, 0.60 g). The resulting colorless solution was composed of 1.3 wt % $\{ZnIn_{2.0}Ga_{1.0}[OCH_2CH_2OCH(CH_3)_2]_{11}\}_n$.

(h) IGZO Ink 2.2%: An ink suitable for formation of an IGZO film with the formula $In_{2.0}Ga_{1.0}ZnO_{5.5}$ (In/Ga/Zn=2:1:1) was prepared by dissolution of $\{ZnIn_{2.0}Ga_{1.0}[OCH_2CH_2OCH(CH_3)_2]_{11}\}_n$ (0.075 g, 0.0502 mmol) in a mixture of p-xylene (3.021 g) and $HOCH_2CH_2OCH(CH_3)_2$ (0.30 mL, 0.27 g). The resulting colorless solution was composed of 2.2 wt % $\{ZnIn_{2.0}Ga_{1.0}[OCH_2CH_2OCH(CH_3)_2]_{11}\}_n$.

(i) IGZO Ink 4.0%: An ink suitable for formation of an IGZO film with the formula $In_{2.0}Ga_{1.0}ZnO_{5.5}$ (In/Ga/Zn=2:1:1) was prepared by dissolution of $\{ZnIn_{2.0}Ga_{1.0}[OCH_2CH_2OCH(CH_3)_2]_{11}\}_n$ (0.436 g, 0.29 mmol) in a mixture of p-xylene (6.888 g) and $HOCH_2CH_2OCH(CH_3)_2$ (4.08 mL, 3.69 g). The resulting colorless solution was composed of 4.0 wt % $\{ZnIn_{2.0}Ga_{1.0}[OCH_2CH_2OCH(CH_3)_2]_{11}\}_n$.

(j) IGZO Ink 5.2%: An ink suitable for formation of an IGZO film with the formula $In_{2.0}Ga_{1.0}ZnO_{5.5}$ (In/Ga/Zn=2:1:1) was prepared by dissolution of $\{ZnIn_{2.0}Ga_{1.0}[OCH_2CH_2OCH(CH_3)_2]_{11}\}_n$ (0.133 g, 0.088 mmol) in a mixture of p-xylene (1.799 g) and $HOCH_2CH_2OCH(CH_3)_2$ (0.70 mL, 0.63 g). The resulting colorless solution was composed of 5.2 wt % $\{ZnIn_{2.0}Ga_{1.0}[OCH_2CH_2OCH(CH_3)_2]_{11}\}_n$.

(k) IGZO Ink 10.5%: An ink suitable for formation of an IGZO film with the formula $In_{2.0}Ga_{1.0}ZnO_{5.5}$ (In/Ga/Zn=2:1:1) was prepared by dissolution of $\{ZnIn_{2.0}Ga_{1.0}[OCH_2CH_2OCH(CH_3)_2]_{11}\}_n$ (0.157 g, 0.105 mmol) in a mixture of p-xylene (0.698 g) and $HOCH_2CH_2OCH(CH_3)_2$ (0.70 mL, 0.63 g). The resulting colorless solution was composed of 10.5 wt % $\{ZnIn_{2.0}Ga_{1.0}[OCH_2CH_2OCH(CH_3)_2]_{11}\}_n$.

Example 20

Thin Film IGZO Materials Made with 1:1:1 In/Ga/Zn Molecular Precursor Compound Ink Formulations A borosilicate glass substrate (50×50×0.6 $mm^3$) was completely covered by 1.0 mL of an ink composed of $ZnIn_{1.0}Ga_{1.0}[OCH_2CH_2OCH(CH_3)_2]_8$ which had been filtered through a 0.2 µm syringe filter. The substrate was then spun at 1158 rpm for 41 s. The resulting $\{ZnIn_{1.0}Ga_{1.0}[OCH_2CH_2OCH(CH_3)_2]_8\}_n$ film was heated in air at 300° C. (hot plate) for 10 min to afford the targeted $In_{1.0}Ga_{1.0}ZnO_4$ material film with a thickness of ~33 nm (profilometry). Digestion of a portion of the resulting film in 70% $HNO_3$, followed by dilution with de-ionized water and analysis by use of ICP found that the In/Ga/Zn ratio of the film was 0.9:0.9:1.0.

Additional inks were spin coated in a similar manner, providing IGZO $In_{1.0}Ga_{1.0}ZnO_{4.0}$ thin films with average thicknesses of 76 nm, 117 nm, 161 nm, 59 nm, 96 nm, and 78 nm, respectively.

Figure 5:
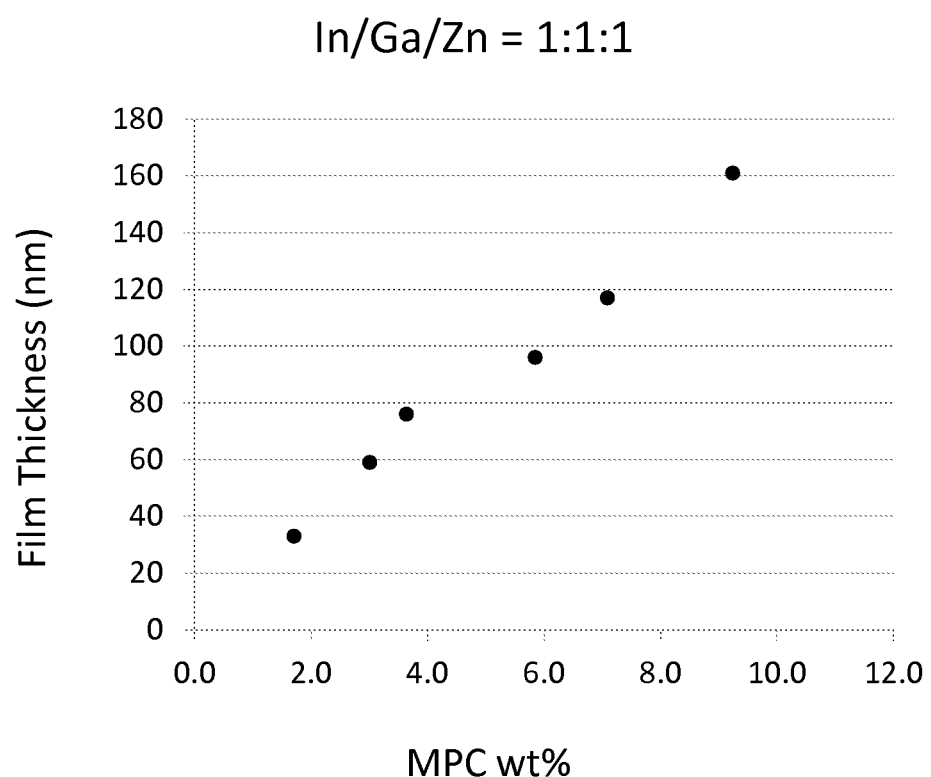
FIG. 5 shows the thickness of IGZO films made by depositing inks, each ink made from an IGZO molecular precursor compound (MPC) having a ratio of In/Ga/Zn of 1:1:1 at several different concentrations. The thickness of the spin-coated films ranged from about 30 to about 160 nm and was proportional to, and controlled by the concentration of the molecular precursor compound, $InGaZn(OCH_2CH_2OCH(CH_3)_2)_8$, in the ink.

As shown in FIG. 5, the film thickness from a single deposition of ink was proportional to, and controlled by the concentration of the molecular precursor $InGaZn(OCH_2CH_2OCH(CH_3)_2)_8$ in the ink.

Example 21

Thin Film IGZO Materials Made with 2:1:1 Molecular Precursor Compound Ink Formulations A borosilicate glass substrate (50×50×0.6 $mm^3$) was completely covered by 1.0 mL of an ink composed of $ZnIn_{2.0}Ga_{1.0}[OCH_2CH_2OCH(CH_3)_2]_{11}$ which had been filtered through a 0.2 µm syringe filter. The substrate was then spun at 1158 rpm for 41 s. The resulting $\{ZnIn_{2.0}Ga_{1.0}[OCH_2CH_2OCH(CH_3)_2]_{11}\}_n$ film was heated in air at 300° C. (hot plate) for 10 min to afford the targeted film of $In_{2.0}Ga_{1.0}ZnO_{5.5}$ material with an average thickness of 17 nm (by use of profilometry).

Additional inks were spin coated in a similar manner, providing $In_{2.0}Ga_{1.0}ZnO_{5.5}$ films with average thicknesses of 30 nm, 40 nm, 74 nm, and 129 nm, respectively.

Figure 6:
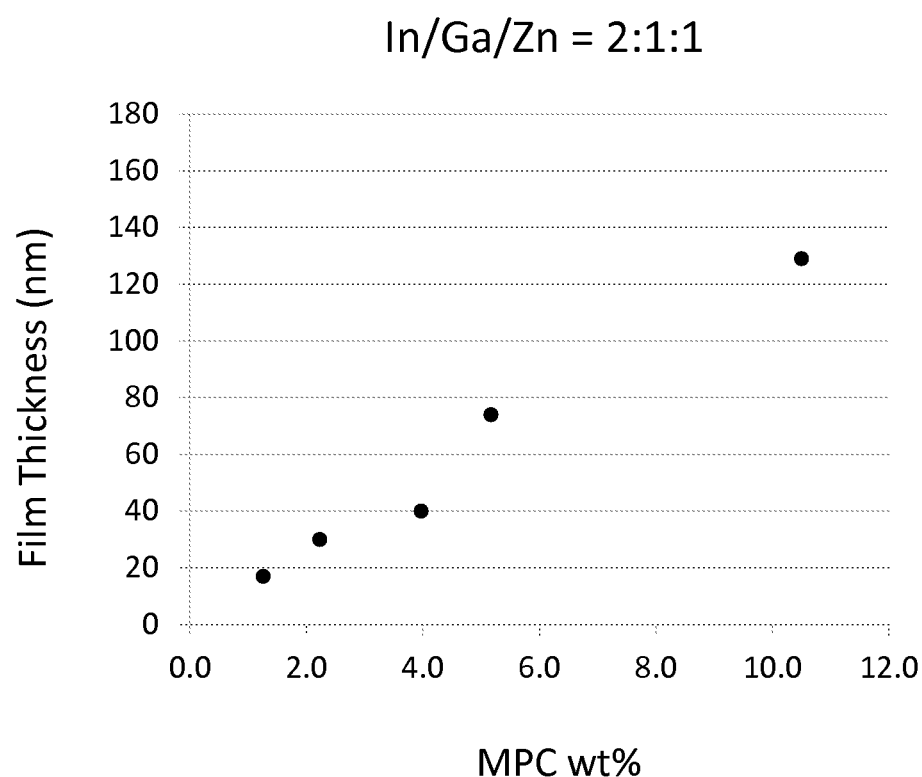
FIG. 6 shows the thickness of IGZO films made by depositing inks, each ink made from an IGZO molecular precursor compound (MPC) having a ratio of In/Ga/Zn of 2:1:1 at several different concentrations. The thickness of the spin-coated films ranged from about 20 to about 130 nm and was proportional to, and controlled by the concentration of the molecular precursor compound, $In_2GaZn(OCH_2CH_2OCH(CH_3)_2)_{11}$, in the ink.

As shown in FIG. 6, the film thickness from a single deposition of ink was proportional to, and controlled by the concentration of the molecular precursor compound $In_{2.0}Ga_{1.0}Zn(OCH_2CH_2OCH(CH_3)_2)_{11}$ in the ink.

Example 22

IGZO Thin Film Materials Made with Molecular Precursor Compound Inks (a) Target material $In_{3.0}Ga_{1.0}ZnO_7$: An ink suitable for formation of an IGZO film with the targeted formula $In_{3.0}Ga_{1.0}ZnO_7$ was prepared by dissolution of $\{ZnIn_{3.0}Ga_{1.0}[OCH_2CH_2OCH(CH_3)_2]_{14}\}_n$ (0.159 g) in a mixture of octane (1.75 g) and $HOCH_2CH_2OCH(CH_3)_2$ (0.94 mL, 0.85 g). The resulting colorless solution was composed of 5.8 wt % $\{ZnIn_{3.0}Ga_{1.0}[OCH_2CH_2OCH(CH_3)_2]_{14}\}_n$.

In an inert atmosphere glove box, a borosilicate glass substrate (50×50×0.6 $mm^3$) was completely covered by 1.0 mL of the above ink which had been filtered through a 0.2 µm syringe filter. The substrate was then spun at 1158 rpm for 40 s. The resulting $\{ZnIn_{3.0}Ga_{1.0}[OCH_2CH_2OCH(CH_3)_2]_{14}\}_n$ film was then heated in air at 300° C. (hot plate) for 20 min to afford the targeted $In_{3.0}Ga_{1.0}ZnO_7$ material film with a thickness of 44 nm (profilometry).

Digestion of a portion of the resulting film in 70% $HNO_3$, followed by dilution with de-ionized water and analysis by use of ICP found that the In/Ga/Zn ratio of the film was 2.90:1.0:1.0.

(b) Target material $In_{1.9}Ga_{0.95}ZnO_{5.3}$: An ink suitable for formation of an IGZO film with the targeted formula $In_{1.9}Ga_{0.95}ZnO_{5.3}$ was prepared by dissolution of $\{ZnIn_{1.9}Ga_{0.95}[OCH_2CH_2OCH(CH_3)_2]_2[OCHCH_3CH_2OC(CH_3)_3]_{8.6}\}_n$ (0.131 g) in octane (1.39 g). The resulting colorless solution was composed of 8.2 wt % $\{ZnIn_{1.9}Ga_{0.95}[OCH_2CH_2OCH(CH_3)_2]_2[OCHCH_3CH_2OC(CH_3)_3]_{8.6}\}_n$.

In an inert atmosphere glove box, a borosilicate glass substrate (50×50×0.6 mm$^3$) was completely covered by 0.8 mL of the above ink which had been filtered through a 0.2 μm syringe filter. The substrate was then spun at 1158 rpm for 40 s. The resulting $\{ZnIn_{1.9}Ga_{0.95}[OCH_2CH_2OCH(CH_3)_2]_2[OCHCH_3CH_2OC(CH_3)_3]_{8.6}\}_n$ film was then heated in air at 300° C. (hot plate) for 20 min to afford the targeted $In_{1.9}Ga_{0.95}ZnO_{5.3}$ material film with a thickness of 28 nm (profilometry).

Digestion of a portion of the resulting film in 70% $HNO_3$, followed by dilution with de-ionized water and analysis by use of ICP found that the In/Ga/Zn ratio of the film was 2.1:1.1:1.0.

Example 23

TFT Device Array Prepared with a 1:1:1 IGZO Molecular Precursor Compound

Figure 7:
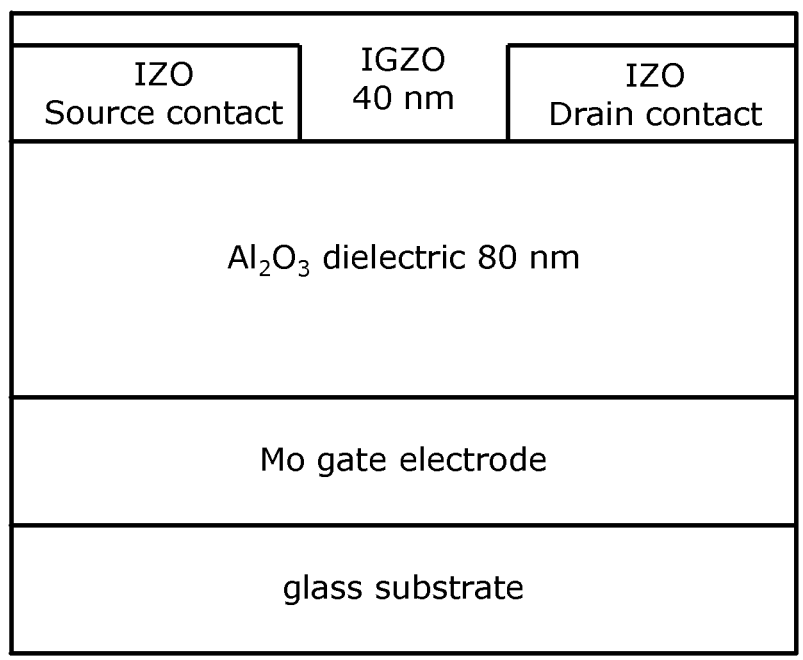
FIG. 7 shows the structure of a TFT device in an array that was prepared with an IGZO molecular precursor compound ink having the ratio In/Ga/Zn of 1:1:1.

A TFT array was prepared with a molecular precursor compound ink having the ratio In/Ga/Zn of 1:1:1. The structure of a device in the completed array is shown in FIG. 7.

Patterned molybdenum metal appropriate for formation of the gate electrode in a TFT array was deposited on a 50×50×0.6 mm$^3$ borosilicate glass slide. Deposition of $Al_2O_3$ (~80 nm) followed by chemical etching led to formation of a patterned gate insulator array. The source and drain electrode array was formed via deposition of indium zinc oxide (reactive sputtering) and subsequent chemical etching. The gate-insulator-source/drain structure was then brought into an inert atmosphere glove box where the molecular precursor compound ink having In/Ga/Zn stoichiometry of 1:1:1 was deposited via spin coating followed by removal from the glove box into ambient air. No IGZO patterning was done. The molecular precursor film was then heated at 300° C. for 10 min in air resulting in formation of a 40 nm indium gallium zinc oxide film. The finished TFT device array was activated by heating at 400° C. for 2 h in air.

Electrical characterization measurements were performed using a probe station and Agilent 4156B parameter analyzer. A 100/10 (width/length) device with a saturation mobility ($\mu_{sat}$) of 11.2 cm$^2$/Vs, threshold voltage ($V_{th}$) of 8.7 V, a subthreshold voltage swing (S) of 0.86 V/dec, and an on/off ratio of ~10$^5$ was obtained.

Example 24

TFT Device Array Prepared with a 2:1:1 IGZO Molecular Precursor Compound

A TFT array was prepared with a molecular precursor compound ink having the ratio In/Ga/Zn of 2:1:1. The structure of a device in the completed array is shown in FIG. 7, except that the $Al_2O_3$ dielectric had a thickness of 200 nm.

Patterned molybdenum metal appropriate for formation of the gate electrode in a TFT array was deposited on a 50×50×0.6 mm$^3$ borosilicate glass slide. Subsequent deposition of $Al_2O_3$ (~200 nm) followed by chemical etching led to formation of the patterned gate insulator array. The source and drain electrode array was formed via deposition of indium zinc oxide (reactive sputtering) and subsequent chemical etching. The gate-insulator-source/drain structure was then brought into an inert atmosphere glove box where a molecular precursor compound ink having In/Ga/Zn stoichiometry of 2:1:1 was deposited via spin coating followed by removal from the glove box into ambient air. No IGZO patterning was done. The molecular precursor film was then heated at 300° C. for 10 min in air resulting in formation of a 40 nm indium gallium zinc oxide film. The finished TFT device array was activated by heating at 400° C. for 2 h in air.

Electrical characterization measurements were performed using a probe station and Agilent 4156B parameter analyzer. A 100/10 (width/length) device with a saturation mobility ($\mu_{sat}$) of 17.0 cm$^2$/Vs, threshold voltage ($V_{th}$) of 1.5 V, a subthreshold voltage swing (S) of 0.23 V/dec, and an on/off ratio of ~10$^6$ was obtained.

A second 100/10 device was characterized and had a saturation mobility ($\mu_{sat}$) of 20.8 cm$^2$/Vs, threshold voltage ($V_{th}$) of 1.4 V, a subthreshold voltage swing (S) of 0.23 V/dec, and an on/off ratio of ~10$^6$.

What is claimed is:

1. An isolated molecular precursor compound having the empirical formula $In_bGa_cZn(OROR)_{3(b+c)+2}$, wherein b and c are each independently from 0.01 to 9.99, the sum of b+c is from 0.02 to 10, and each R is independently alkyl or aryl.

2. The compound of claim 1, wherein the R groups are independently selected, for each occurrence, from C(1-6) alkyl groups.

3. The compound of claim 1, wherein the R groups are independently selected, for each occurrence, from ethyl, n-propyl, isopropyl, n-butyl, sec-butyl, isobutyl, t-butyl, isopentyl, 2-methylbutyl, 3-methylbutyl, 2,2-dimethylbutyl, 2,3-dimethylbutyl, 2-methylpentyl, 3-methylpentyl, and 4-methylpentyl.

4. The compound of claim 1, wherein the R groups are independently selected, for each occurrence, from C(2-4) alkyl groups.

5. An ink comprising a molecular precursor compound of claim 1 and one or more solvents.

6. The ink of claim 5, wherein the ink further comprises one or more dopant elements selected from halides, Mg, Y, Ti, Zr, Nb, Cr, Ru, Bi, Sb, and La.

7. A process for making a material, the process comprising:
providing an ink comprising one or more molecular precursor compounds according to claim 1;
depositing the ink on a substrate; and
heating the substrate.

8. The process of claim 7, wherein the ratio of (In+Ga) to Zn in the ink is from 0.02 to 10.

9. The process of claim 7, wherein the heating is at a temperature of from 50° C. to 500° C.

10. The process of claim 7, wherein the heating is performed in air having controlled humidity.

11. The process of claim 7, wherein the depositing is done with an ink by printing, inkjet printing, aerosol jet printing, gravure printing, reverse gravure printing, reverse offset gravure printing, stamp printing, transfer printing, pad printing, spray pattern printing, flexographic printing, contact printing, reverse printing, thermal printing, lithography, electrophotographic printing, screen printing, spraying, spray coating, spray deposition, spray pyrolysis, coating, dip coating, wet coating, spin coating, knife coating, roller coating, rod coating, slot die coating, meyerbar coating, lip direct coating, capillary coating, liquid deposition, solution deposition, layer-by-layer deposition, spin casting, and solution casting.

12. The process of claim 7, wherein the substrate is a glass, a ceramic, or a polymer.

13. An indium gallium zinc oxide (IGZO) material made by the process of claim 7.

14. A thin film transistor comprising the IGZO material of claim 13.

15. A process for making a material, the process comprising:
providing an ink that comprises a molecular precursor compound according to claim 1 by dissolving monomer compounds $Zn(Q)_2$, $In(Q)_3$, and $Ga(Q)_3$, wherein Q is —OROR, and wherein each R is independently alkyl or aryl;
depositing the ink on a substrate; and
heating the substrate.

16. The process of claim 15, wherein the R groups are independently selected, for each occurrence, from C(1-6) alkyl groups.

17. The process of claim 15, wherein the R groups are independently selected, for each occurrence, from ethyl, n-propyl, isopropyl, n-butyl, sec-butyl, isobutyl, t-butyl, isopentyl, 2-methylbutyl, 3-methylbutyl, 2,2-dimethylbutyl, 2,3-dimethylbutyl, 2-methylpentyl, 3-methylpentyl, and 4-methylpentyl.

18. The process of claim 15, wherein the R groups are independently selected, for each occurrence, from C(2-4) alkyl groups.

19. The process of claim 15, wherein the heating is at a temperature of from 50° C. to 500° C.

20. The process of claim 15, wherein the heating is performed in air having controlled humidity.

21. The process of claim 15, wherein the ink further comprises one or more dopant elements selected from halides, Mg, Y, Ti, Zr, Nb, Cr, Ru, Bi, Sb, and La.

22. The process of claim 15, wherein the depositing is done with an ink by printing, inkjet printing, aerosol jet printing, gravure printing, reverse gravure printing, reverse offset gravure printing, stamp printing, transfer printing, pad printing, spray pattern printing, flexographic printing, contact printing, reverse printing, thermal printing, lithography, electrophotographic printing, screen printing, spraying, spray coating, spray deposition, spray pyrolysis, coating, dip coating, wet coating, spin coating, knife coating, roller coating, rod coating, slot die coating, meyerbar coating, lip direct coating, capillary coating, liquid deposition, solution deposition, layer-by-layer deposition, spin casting, and solution casting.

23. The process of claim 15, wherein the substrate is a glass, a ceramic, or a polymer.

24. An IGZO material made by the process of claim 15.

25. A thin film transistor comprising the IGZO material of claim 24.

* * * * *